(12) United States Patent
Schunk

(10) Patent No.: US 11,957,761 B2
(45) Date of Patent: Apr. 16, 2024

(54) COMPOUNDS HAVING α4β7 INTEGRIN INHIBITION ACTIVITY

(71) Applicant: Zealand Pharma A/S, Søborg (DK)

(72) Inventor: Stefan Schunk, Søborg (DK)

(73) Assignee: Zealand Pharma A/S, Søborg (DK)

( * ) Notice: Subject to any disclaimer, the term of this patent is extended or adjusted under 35 U.S.C. 154(b) by 0 days.

(21) Appl. No.: 18/068,657

(22) Filed: Dec. 20, 2022

(65) Prior Publication Data
US 2023/0190946 A1 Jun. 22, 2023

(30) Foreign Application Priority Data

| | | |
|---|---|---|
| Dec. 20, 2021 | (EP) | 21216012.1 |
| Oct. 13, 2022 | (EP) | 22201323.7 |
| Dec. 19, 2022 | (TW) | 111148705 |

(51) Int. Cl.
| | |
|---|---|
| *A61K 47/64* | (2017.01) |
| *A61K 47/54* | (2017.01) |
| *A61P 1/12* | (2006.01) |
| *A61P 29/00* | (2006.01) |

(52) U.S. Cl.
CPC ............ *A61K 47/64* (2017.08); *A61K 47/545* (2017.08); *A61P 1/12* (2018.01); *A61P 29/00* (2018.01)

(58) Field of Classification Search
CPC ................................. A61K 38/12; A61K 47/64
See application file for complete search history.

(56) References Cited

U.S. PATENT DOCUMENTS

| | | | |
|---|---|---|---|
| 4,818,771 A | 4/1989 | Toda et al. | |
| 2022/0411408 A1 | 12/2022 | Xing et al. | |

FOREIGN PATENT DOCUMENTS

| | | |
|---|---|---|
| CN | 110862380 A | 3/2020 |
| WO | WO-2017/079821 A1 | 5/2017 |
| WO | WO-2018/085921 A1 | 5/2018 |
| WO | WO-2018/205008 A1 | 11/2018 |
| WO | WO-2021/078022 A1 | 4/2021 |
| WO | WO-2022/002781 A1 | 1/2022 |

OTHER PUBLICATIONS

Soler-Ferran et al., "Integrin 47 Antagonists: Activities, Mechanisms of Action and Therapeutic Prospects", Current Immunology Reviews, 2012, 118-134 (Year: 2012).*

(Continued)

*Primary Examiner* — Lianko G Garyu
(74) *Attorney, Agent, or Firm* — MARSHALL, GERSTEIN & BORUN LLP

(57) ABSTRACT

Compounds of formula (1):

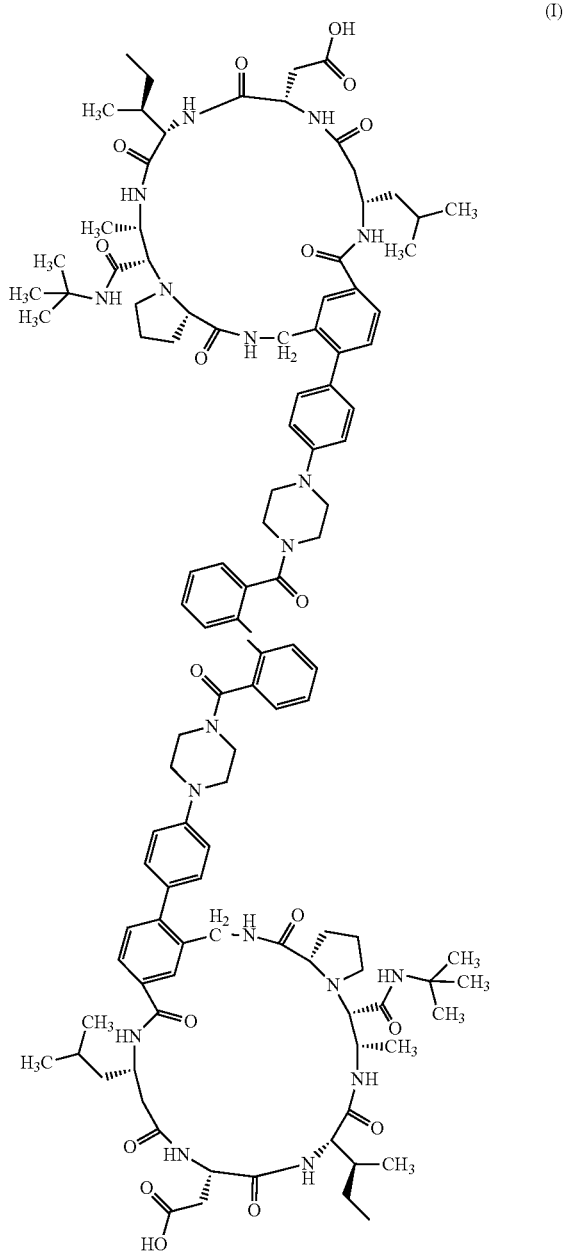

(I)

and pharmaceutically acceptable salts and solvates thereof, are described. The compounds are α4β7 antagonists and are useful in the prevention or treatment of inflammatory conditions and/or autoimmune diseases, especially inflammatory bowel disease.

2 Claims, 9 Drawing Sheets

(56) References Cited

OTHER PUBLICATIONS

Soler-Ferran et al., "Integrin a4b7 Antagonists: Activities, Mechanisms of Action and Therapeutic Prospects", Current Immunology Reviews, 2012, 118-134 (Year: 2012).*
Johns Hopkins Medicine—Pathology, "Classification of Autoimmune Diseases", https://pathology.jhu.edu/autoimmune/classification, obtained 2023 (Year: 2023).*
Lynch et al., "The Use of Biologics in Patients with Inflammatory Bowel Disease and Primary Sclerosing Cholangitis", Current Hepatology Reports, 2019, 115-126 (Year: 2019).*
The American Museum of Natural History, "What about Other Diseases? Challenges to Disease Eradication", https://www.amnh.org /explore/science-topics/disease-eradication/countdown-to-zero/what-about-other-diseases, 2012 (Year: 2012).*
Arthos et al., The Role of Integrin a4b7 in HIV Pathogenesis and Treatment:, Current HIV/AIDS Reports, 2018, 127-135 (Year: 2018).*
Johnson et al., "Early treatment with anti-a4b7 antibody facilitates increased gut macrophage maturity in SIV-infected rhesus macaques", Frontiers in Immunology, 2022, 16 pages (Year: 2022).*
Ziani et al., "Mucosal integrin a4b7 blockade fails to reduce the seeding and size of viral reservoirs in SIV-infected rhesus macaques", The FASEB Journal, 2021, 11 pages (Year: 2021).*
Center for Disease Control and Prevention, "Vaccine-Preventable Diseases", https://www.cdc.gov/globalhealth/immunization/diseases/index.html#print, updated on Jun. 15, 2023. (Year: 2023).*
Lieberman, H. A et al., "Pharmaceutical Dosage Forms", Tablets, Marcel Dekker, Inc., vol. 1, 1st Edition, 4 pages (1980).
"Remington: Practice of the Science and Pharmacy", Mack Publishing Company, vol. 1, 19th Edition, 45 pages (1995).
"Remington: Practice of the Science and Pharmacy", Mack Publishing Company, vol. 2, 19th Edition, 38 pages (1995).
Greene, T. W et al., "Protective Groups in Organic Synthesis", John Wiley & Sons, Inc., 3rd Edition, Chapter 2, 231 pages (1999).
Greene, T. W et al., "Protective Groups in Organic Synthesis", John Wiley & Sons, Inc., 3rd Edition, Chapter 5, 87 pages (1999).
Greene, T. W et al., "Protective Groups in Organic Synthesis", John Wiley & Sons, Inc., 3rd Edition, Chapter 7, 162 pages (1999).
Greene, T. W et al., "Protective Groups in Organic Synthesis", John Wiley & Sons, Inc., 3rd Edition, Chapter 7, 28 pages (1999).
Kates, S. A et al., "Solid-Phase Synthesis", A Practical Guide, Marcel Dekker, Inc., Chapter 2, 28 pages (2000).
Kates, S. A et al., "Solid-Phase Synthesis", A Practical Guide, Marcel Dekker, Inc., Chapter 3, 30 pages (2000).
Kates, S. A et al., "Solid-Phase Synthesis", A Practical Guide, Marcel Dekker, Inc., Chapter 4, 71 pages (2000).
Kates, S. A et al., "Solid-Phase Synthesis", A Practical Guide, Marcel Dekker, Inc., Chapter 5, 81 pages (2000).
Kates, S. A et al., "Solid-Phase Synthesis", A Practical Guide, Marcel Dekker, Inc., Chapter 6, 60 pages (2000).
Kates, S. A et al., "Solid-Phase Synthesis", A Practical Guide, Marcel Dekker, Inc., Chapter 7, 38 pages (2000).
Liang, A. C et al., "Fast-Dissolving Intraoral Drug Delivery Systems", Expert Opin. Ther. Patents,, 7 pages (2001).
Nishitani, Y et al., "Lactococcus Lactis Subsp. Cremoris FC Alleviates Symptoms of Colitis Induced By Dextran Sulfate Sodium in Mice", Int. Immunopharmacol., 9:1444-1451 (2009).
Bang, B et al., "Methods of Inducing Inflammatory Bowel Disease in Mice", Curr. Protocl. in Pharmacol., 72:5.58.1-5.58.42, 42 pages (Mar. 2016).
EPO Extended Search Report in European patent appl. No. EP 21 21 6012, dated May 13, 2022, 6 pages.
International Search Report and Written Opinion in PCT/EP2022/086854 (12 pages) (Jan. 31, 2023).
Yoosuf et al., "Evolving Therapy for Celiac Disease", Frontiers in Pediatrics, vol. 7, Article 193, May 2019, 18 pages.
Cushing et al., "Vedolizumab as a Novel Treatment for Refractory Collagenous Colitis: A Case Report", The American Journal of Gastroenterology, vol. 113, Apr. 2018, pp. 632-633.
Kim et al., "Vedolizumab Treatment May Reduce Steroid Burden and Imrove Histology in Patients With Eosinophilic Gastroenteritis", Clin Gastroenterol Hepatol, vol. 16, No. 12, Dec. 2018, pp. 1992-1994.
Chen et al., "Vedolizumab for Prevention of Graft-versus-host Disease After Allogeneic Hematopoietic Stem Cell Transplantation", Blood Advances, vol. 3, No. 23, Dec. 10, 2019, pp. 4136-4146.
Jennings et al., "Vedolizumab-induced Remission in 3 Patients With Refractory Microscopic Colitis: A Tertiary Care Center Case Series", Inflamm Bowel Dis, vol. 25, No. 8, Aug. 2019, 1 page.
Ribaldone et al., "Vedolizumab for Treatment of Chronic Refractory Pouchitis: a Systematic Review With Pool Analysis", Rev Esp Enferm Dig, vol. 112, No. 1, 2020, pp. 59-63.
Takeda Pharmaceuticals America, Inc. ENTYVIO - Vedolizumab Injection, Powder, Lyophilized, for Solution Revised label, Oct. 2022, 26 pages.

* cited by examiner

COMPOUNDS HAVING α4β7 INTEGRIN INHIBITION ACTIVITY

FIELD OF THE INVENTION

This invention relates to novel compounds. The invention also relates to their preparation, and their use in the treatment of a number of conditions mediated by α4β7 integrin, particularly although not exclusively inflammatory conditions and/or autoimmune diseases, such as inflammatory bowel diseases.

BACKGROUND TO THE INVENTION

Integrins are transmembrane receptors that are the bridges for cell-cell and cell-extracellular matrix (ECM) interactions. They are involved in numerous cellular processes, including cell adhesion and migration, and regulating gene expression.

Integrins are obligate heterodimers, having two different chains: the α (alpha) and β (beta) subunits. The α4β7 integrin is expressed on lymphocytes and is responsible for T-cell homing into gut-associated lymphoid tissues through its binding to mucosal addressin cell adhesion molecule 1 (MAdCAM-1), which is present on high endothelial venules of mucosal lymphoid organs.

Inhibitors of specific integrin-ligand interactions have been shown effective as anti-inflammatory agents for the treatment of various autoimmune diseases. For example, monoclonal antibodies displaying high binding affinity for α4β7 have displayed therapeutic benefits for gastrointestinal auto-inflammatory/autoimmune diseases, such as Crohn's disease, and ulcerative colitis.

WO2022/002781, which was published after the earliest priority date of the present application, discloses a compound which exhibits α4β7 integrin antagonist activity. This compound is referred to as "Comparative Compound 1" in the Examples described herein.

There is a need to develop improved α4β7 antagonists to prevent or treat inflammatory conditions and/or autoimmune diseases.

SUMMARY OF THE INVENTION

In one aspect of the invention, there is provided a compound of formula (I):

(I)

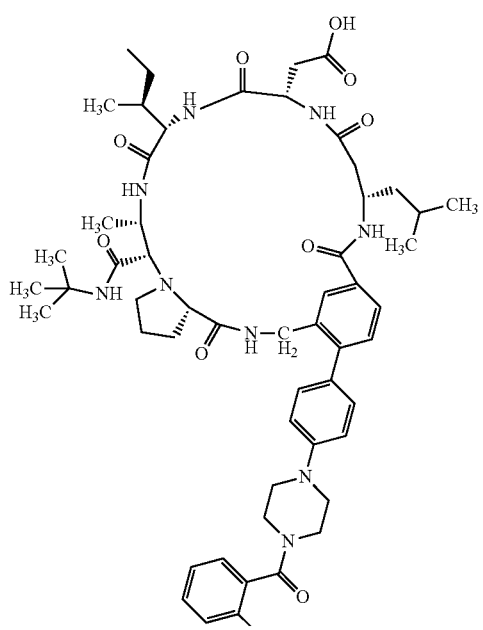

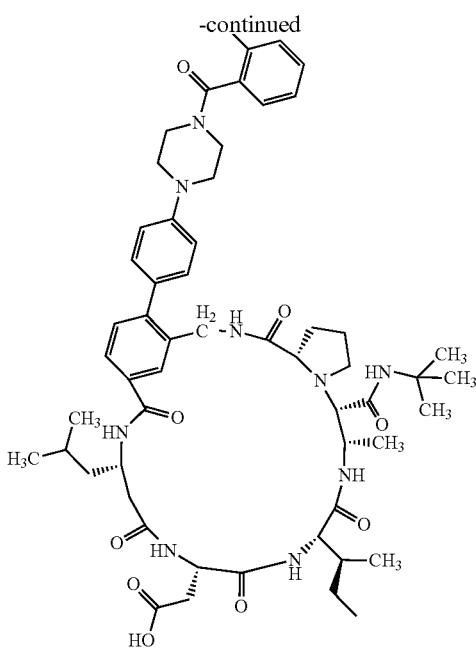

or a pharmaceutically acceptable salt or solvate thereof.

In another aspect, the invention provides a pharmaceutical composition comprising the compound of formula (I), or a pharmaceutically acceptable salt or solvate thereof, and a pharmaceutically acceptable carrier.

In another aspect, the invention provides the compound of formula (I), or a pharmaceutically acceptable salt or solvate thereof, for use as a medicament.

In another aspect, the invention provides the compound of formula (I), or a pharmaceutically acceptable salt or solvate thereof, for use in treating an inflammatory condition and/or an autoimmune disease in a patient.

In another aspect, the invention provides use of the compound of formula (I), or a pharmaceutically acceptable salt or solvate thereof, in the manufacture of a medicament for treating an inflammatory condition and/or an autoimmune disease in a patient.

In another aspect, the invention provides a method of treating an inflammatory condition and/or an autoimmune disease in a patient in need thereof, the method comprising administration of the compound of formula (I), or a pharmaceutically acceptable salt or solvate thereof, to the patient.

ADVANTAGES AND SURPRISING FINDINGS

Figure 1:
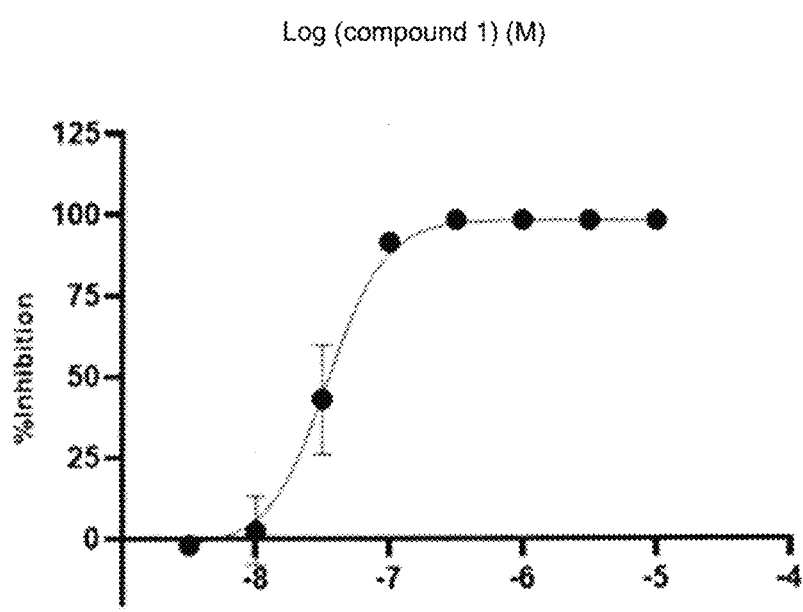
FIG. 1 shows the dose-response curve for compound 1.

The compounds of formula (I), specifically compound 1, as described herein, has been surprisingly found by the present inventors to be more chemically stable than comparative compound 1 as described in more detail below. In particular, compound 1 has been demonstrated to be more stable in both aqueous and dry formulations than comparative compound 1. This finding was unexpected as it could not have been predicted from the art that a single amino acid substitution would lead to such a significant increase in stability.

The compounds of formula (I), specifically compound 1, as described herein, has also been found by the present inventors to exhibit an unexpectedly long half-life when dosed in vivo, compared with comparative compound 1 as described in more detail below. This would not have been expected in view of the small structural difference between the compounds.

The compounds of formula (I), specifically compound 1, as described herein, has also been surprisingly found by the present inventors to be more chemically stable than comparative compound 2 as described in more detail below.

DETAILED DESCRIPTION

In one aspect of the invention, there is provided a compound of formula (I), as defined above, or a pharmaceutically acceptable salt or solvate thereof. In this specification all references to compounds of formula (I) generally include references to pharmaceutically acceptable salts and solvates thereof.

In certain embodiments, there is provided according to the invention pharmaceutically acceptable salts of the compounds described herein. The term "pharmaceutically acceptable salt" as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by treatment of the compound with a suitable acid, such that one or more nitrogen atoms is protonated, or with a suitable base, such that one or more carboxylic acid groups is deprotonated. Salts also include zwitterionic forms of the compound in which one or more amino groups is protonated and one or more carboxylic acid groups is deprotonated, but no other counter-ions are present.

One representative acid addition salt is the bicarbonate salt. One representative base addition salt is the ammonium salt.

Included within the scope of the present invention are all stereoisomers, geometric isomers and tautomeric forms of the compounds of formula (I), including compounds exhibiting more than one type of isomerism, and mixtures of one or more thereof.

General Synthetic Methods

The compound of formula (I) may be synthesized using the process shown generally in Scheme 1.

Scheme 1
(a1) deprotection then PG$_1$-Ile-OH
(a2) deprotection then PG$_1$-Asp(PG$_2$)-OH
(a3) deprotection then PG$_1$-Leu-OH
(a4) deprotection then
(a5) deprotection
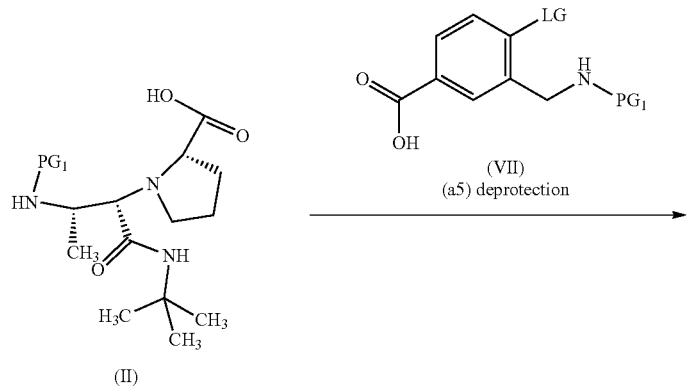
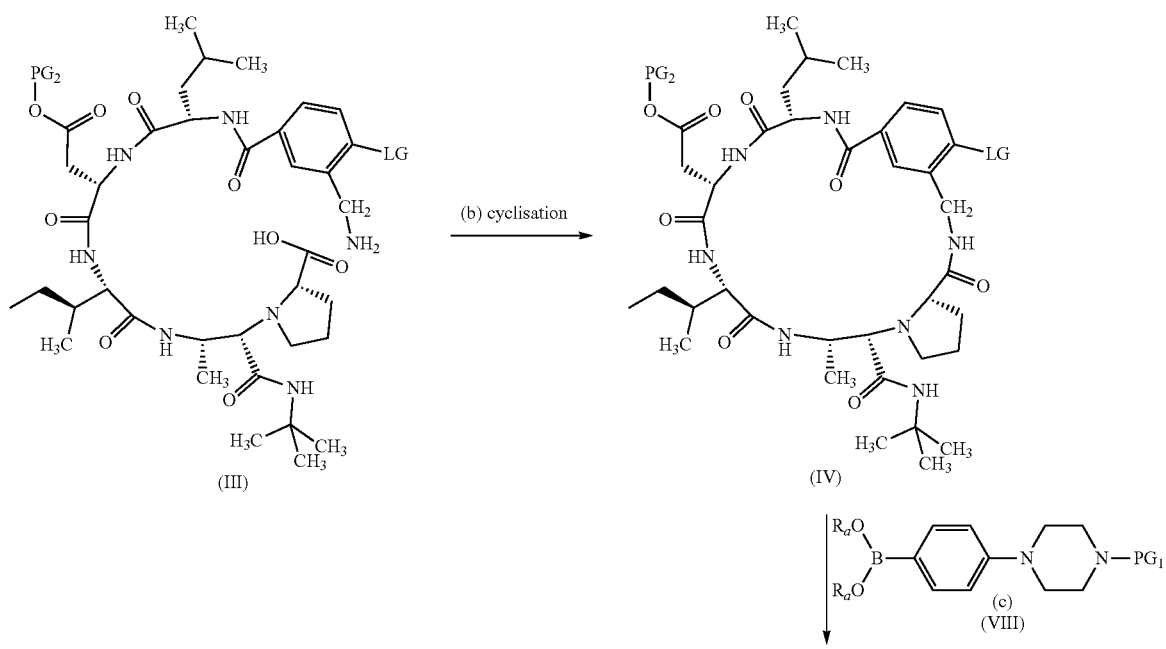

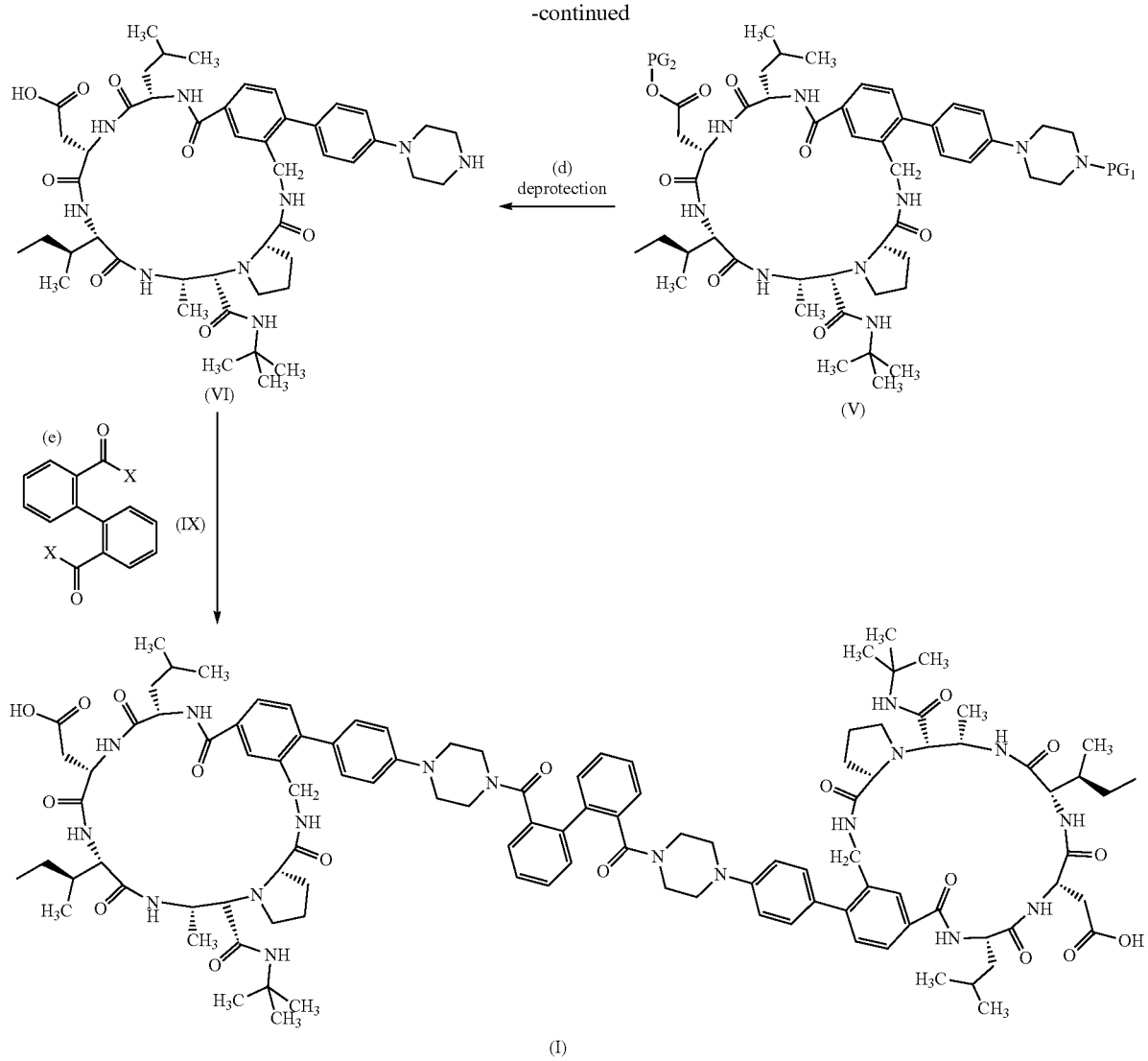

In Scheme 1, the variables have the following meanings:
PG$_1$ is an amino-protecting group;
PG$_2$ is a carboxy-protecting group;
LG is a leaving group;
X is a leaving group or a group convertible to a leaving group; and each R$_a$ is C$_{1-6}$ alkyl, or the two groups R$_a$ together form a C$_{1-6}$ alkylene group optionally fused to an aryl group.

There is no particular limitation to the nature of each of the protecting groups PG$_1$ and PG$_2$ provided that they fulfil the normal function of a protecting group, i.e. that they can be attached to the relevant group, remain attached so as to protect that group from any subsequent reaction to which they may be labile, and can be removed when protection is no longer required.

The protecting groups PG$_1$ and PG$_2$ are well known to those skilled in the art. Suitable examples are described in "Protective Groups in Organic Synthesis" by T. W. Greene and P. Wuts, Wiley and Sons, 3rd Edition, 1999.

Examples of the amino-protecting group PG$_1$ include the following: carbobenzyloxy (Cbz); p-methoxybenzyl carbonyl (Moz or MeOZ); tert-butyloxycarbonyl (BOC); 9-fluorenylmethyloxycarbonyl (Fmoc) group; acetyl (Ac); benzoyl (Bz); benzyl (Bn); carbamate; p-methoxybenzyl (PMB); 3,4-dimethoxybenzyl; p-methoxyphenyl (PMP); p-toluenesulfonyl (tosyl, Ts); Troc (trichloroethyl chloroformate); p-nitrophenylsulfonyl (nosyl) and o-nitrophenylsulfonyl (Nps) groups. Preferred PG$_1$ groups are BOC and Fmoc.

Examples of the carboxyl-protecting group PG$_2$ include esters, the other moiety of the ester group including branched C$_{3-6}$ alkyl, such as tert-butyl; C$_{3-8}$ cycloalkyl, especially cyclohexyl; benzyl; esters of 2,6-disubstituted phenols (e.g. 2,6-dimethylphenol, 2,6-diisopropylphenol, 2,6-di-tert-butylphenol); silyl esters; and orthoesters. Preferred PG$_3$ groups include branched C$_{3-6}$ alkyl, C$_{5-7}$ cycloalkyl, and benzyl, especially tert-butyl, cyclohexyl and benzyl.

Examples of the leaving group LG include halogen (especially chloro, bromo or iodo) and sulfonate groups (such as methanesulfonate, trifluoromethanesulfonate and p-toluenesulfonate). Preferred are halogen, and especially bromo or iodo.

Examples of the group X are leaving groups, as defined and exemplified above in relation to the group LG. Examples of groups convertible to a leaving group include hydroxyl.

Compound (III) is formed from compound (II) by successive amide coupling reactions (a1) to (a4) with the relevant protected amino acid, followed by a final deprotection step (a5).

Each of the steps (a1) to (a4) is carried out by, firstly, removing the protecting group $PG_1$ from the amino terminus of the starting amino acid, then coupling the resulting amine, with the carboxyl portion of the next amino acid, typically in the presence of a conventional coupling agent, typically in the presence of base, in a suitable solvent. Unless the solid-phase synthetic method referred to below is used, the carboxyl terminus of the compound of formula (II) and the intermediates involved in steps (a1) to (a4) must be protected during these amide coupling steps. Suitable carboxyl-protecting groups are as defined and exemplified above in relation to the group $PG_2$.

Methods for carrying out the deprotection steps (a1) to (a5), and suitable deprotecting agents, are well known to the person skilled in the art. Suitable deprotecting agents are described in "Protective Groups in Organic Synthesis", referred to above. By way of example, when $PG_1$ is Fmoc, the deprotecting agent may be piperidine.

The coupling agent may be any agent which facilitates the coupling of a carboxylic acid and an amine to produce an amide. Examples of coupling agents are also well known to the person skilled in the art. Typical coupling agents include carbodiimides such as diisopropylcarbodiimide (DIC) and dicyclohexylcarbodiimide (DCC); aminium and uronium reagents such as 1-[bis-(dimethylamino)methyliumyl]-1H-1,2,3-triazolo[4,5-b]pyridine-3-oxide hexafluorophosphate (HATU), 2-(1H-benzotriazol-1-yl]-1,1,3,3-tetramethyluronium hexafluorophosphate (HBTU) and O-(1H-6-chlorobenzotriazole-1-yl)-1,1,3,3-tetramethyluronium hexafluorophosphate (HCTU), and organophosphate reagents such as 3-(diethoxyphosphoryloxy)-1,2,3-benzotriazin-4(3H)-one (DEPBT). The coupling agent may also be used in conjunction with an additive such as HOBT (1-hydroxy-benzotriazole) or ethyl cyanohydroxyiminoacetate (Oxyma®). Oxyma and DIC are preferred.

The base is not particularly restricted provided it is capable of acting as a base and does not react with the activated amino acid. Examples of suitable bases include tertiary amines, including trimethylamine, triisopropylamine and diisopropylethylamine. Diisopropylethylamine is preferred.

The solvent is not particularly restricted provided it is inert to the reaction and capable of dissolving the reactants to at least some extent. Examples of suitable solvents include: halogenated hydrocarbons, such as dichloromethane (DCM); dimethyl sulfoxide (DMSO); dimethylformamide (DMF); N-methylpyrrolidone (NMP) and mixtures thereof, of which DMF is preferred.

Advantageously, steps (a1) to (a5) are carried out on a solid phase. The support is typically an organic polymer, typically in the form of a resin, having functional groups capable of reacting with one terminus of the peptide chain to facilitate attachment of this end to the chain. Since the peptide remains covalently attached to the support throughout the synthesis, excess reagents and side products can be removed by washing and filtration.

Typically, this involves reacting compound (II) with a suitable solid support, such that the carboxy terminus of compound (II) is conjugated to the solid support; performing the deprotection part of steps (a1) to (a4) by washing the solid support with a suitable deprotecting agent; carrying out the coupling part of steps (a1) to (a4) as described above; performing the deprotection step (a5) by washing the solid support with a suitable deprotecting agent; and finally cleaving the compound from the solid support to yield the compound of formula (III).

Examples of solid phase peptide synthesis and methods of carrying them out are well known to the person skilled in the art, as taught for example in "Solid Phase Synthesis: A Practical Guide", ed. S. Kates & F. Albericio, CRC Press, 2000.

Examples of organic polymers suitable for forming solid support resins include polystyrene, typically cross-linked polystyrene (obtained by co-polymerisation of styrene and divinylbenzene).

The functional group may be any group which allows linking to the organic polymer while allowing the partially protected peptide chain to be assembled thereon, and can be cleaved under conditions which do not affect the side-chain protecting groups.

Examples of functional groups with which the organic polymer may be functionalized include triarylmethylhalo, preferably tritylhalo (especially tritylchloro); diarylmethylhalo, especially benzhydrylhalo; halobenzyl; and halomethyl. A polymer functionalised with a tritylhalo group, especially 2-chlorotrityl-resin, is preferred as it permits liberation of the partly protected compound of formula (III).

The initial conjugation of compound (II) to a suitable solid support can be carried out by reacting the compound (II) with the functionalised organic polymer which provides the solid support, in a suitable solvent.

For certain resins, especially triarylmethylhalo resins, the reaction may be carried out in the presence of base. The base must be soluble in the solvent. Examples of suitable bases include tertiary amines, including trimethylamine, triisopropylamine and diisopropylethylamine, of which diisopropylethylamine are preferred.

The solvent is not particularly restricted provided it is inert to the reaction, is capable of causing the organic polymer resin to swell therein, and capable of dissolving the reactants to at least some extent. Examples of suitable solvents include those defined and exemplified above in relation to steps (a1) to (a4) and mixtures thereof. DMF is preferred.

The final step of cleaving the compound from the solid support to produce the compound of formula (III) can be carried out using a cleaving agent in a suitable solvent. The cleaving agent is typically an acid, which is strong enough and/or present in sufficient concentration to cleave the compound of formula (III) from the solid support while leaving the protecting groups on the compound intact. Particularly preferred is 1,1,1,3,3,3-hexafluoroisopropanol (HFIP).

The solvent is not particularly restricted provided it is inert to the reaction and capable of dissolving the reactants to at least some extent. Examples of suitable solvents include alcohols, such as methanol, ethanol and isopropanol; halogenated hydrocarbons, such as dichloromethane (DCM) and mixtures thereof. DCM is preferred.

In step (b), compound (IV) is formed by cyclisation of compound (III) in an intramolecular amide coupling reaction, typically in the presence of a conventional coupling agent, typically in the presence of base, in a suitable solvent.

The coupling agent may be any agent which facilitates the coupling of a carboxylic acid and an amine to produce an amide. Examples of coupling agents include those defined and exemplified above in relation to steps (a1) to (a4). HATU is preferred.

The solvent is not particularly restricted provided it is inert to the reaction and capable of dissolving the reactants to at least some extent. Examples of suitable solvents include those defined and exemplified above in relation to steps (a1) to (a4) and mixtures thereof. DMF is preferred.

The reaction is typically carried out under suitable conditions in order that the intramolecular amide coupling required for the cyclisation to take place and result in the compound of formula (IV) predominates over any intermolecular reaction between two molecules of the compound of formula (III). Typically, the reaction is carried out at a dilution between 0.1 mM and 1000 mM, preferably 0.2 to 500 mM, more preferably 10 to 100 mM.

In step (c), compound (V) is formed by reacting compound (IV) with compound (VIII) in an aryl cross-coupling reaction, typically in the presence of a catalyst, typically in the presence of base, in a suitable solvent.

Compounds of formula (VIII) are commercially available. One such commercially available compound is 4-(4-(benzyloxycarbonyl)-piperazino)phenylboronic acid pinacol ester, where $PG_1$ is benzyloxycarbonyl and the two groups $R_a$ together form a 1,1,2,2-dimethylethylene group.

The catalyst may be any catalyst which is able to catalyse the coupling of an aryl halide or aryl sulfonate (e.g. methanesulfonate or trifluoromethanesulfonate) and an aryl boronic ester to form a carbon-carbon bond between two aryl groups. Examples of catalysts include organopalladium reagents and organonickel reagents, of which tetrakis(triphenylphosphine)palladium (0) is preferred.

The reaction is typically carried out in the presence of a base. Examples of suitable bases include alkali metal carbonates such as sodium carbonate or potassium carbonate; alkali metal phosphates, such as sodium phosphate or potassium phosphate; and alkali metal alkoxides, such as sodium ethoxide or potassium ethoxide. Potassium phosphate is preferred.

The solvent is not particularly restricted provided it is inert to the reaction and capable of dissolving the reactants to at least some extent. Examples of suitable solvents include water; alcohols, such as methanol, ethanol and isopropanol; ethers, such as dioxane, 1,2-dimethoxyethane (DME); and mixtures thereof. A mixture of water and dioxane is preferred.

In step (d), compound (VI) is formed from compound (V) by removal of the amino-protecting group $PG_1$ and the carboxy-protecting group $PG_2$. This is carried out in the presence of a suitable deprotecting reagent, typically in a suitable solvent.

Methods for carrying out the deprotection step (d), and suitable deprotecting reagents, are well known to the person skilled in the art. Suitable deprotecting reagents are described in "Protective Groups in Organic Synthesis", referred to above. Examples of suitable deprotecting reagents include strong acids, of which trifluoroacetic acid is preferred.

In step (e), compound (I) is formed by an amide coupling reaction of compound (VI) with compound (IX), typically in the presence of base, in a suitable solvent.

To facilitate the reaction, the compound of formula (IX) where X is OH may first be converted to another compound of formula (IX) where X is a leaving group, such as halide and particularly where X is chloro. This is carried out by reacting the compound of formula (IX) where X is OH with a halogenating agent. Examples of suitable halogenating agents include oxalyl chloride, thionyl chloride, phosphorus trichloride and phosphorus pentachloride, of which oxalyl chloride is preferred.

The base is not particularly restricted provided it is capable of acting as a base and does not react with the compound of formula (IX) where X is a leaving group. Examples of suitable bases include those defined and exemplified above in relation to steps (a1) to (a4). Tertiary amines, especially diisopropylethylamine are preferred.

The compound of formula (VII) may be synthesized using the process shown generally in Scheme 2.

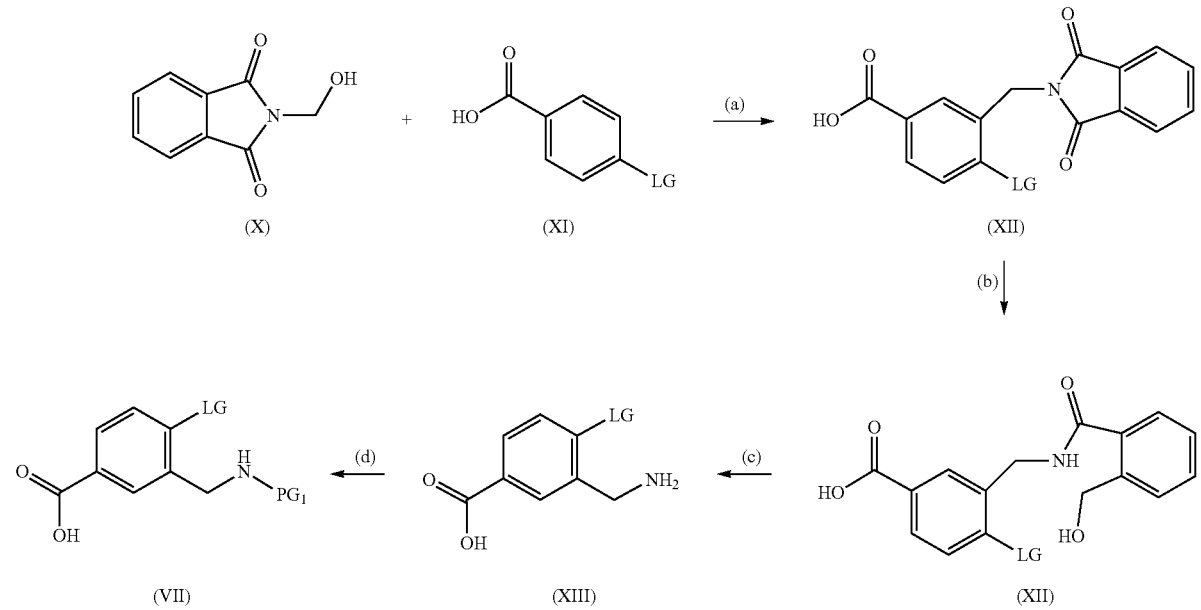

In Scheme 2, LG has the same meaning as in Scheme 1.

In step (a), compound (XII) is formed by reaction of compound (X) with compound (XI), typically in the presence of an acid, in a suitable solvent. Methods for carrying out the reaction step (a), and suitable conditions and reagents, are well known to the person skilled in the art. The compounds of formulae (X) and (XI) are commercially available.

The acid is not particularly restricted provided it is capable of acting as an acid. Strong acids are typically used. Examples of suitable acids include: inorganic acids such as sulfuric acid and nitric acid, and organic acids, especially sulfonic acids such as methanesulfonic acid, trifluoromethanesulfonic acid, benzenesulfonic acid, and p-toluenesulfonic acid. Sulfonic acids are preferred and trifluoromethanesulfonic acid is especially preferred.

The solvent is not particularly restricted provided it is dissolving the reactants to at least some extent. It is particularly preferred in this case that the acid acts as the solvent. Sulfonic acids are preferred and trifluoromethanesulfonic acid is especially preferred.

In step (b), compound (XIII) is formed by reduction of compound (XII) in a suitable solvent. Methods for carrying out the reduction step (b), and suitable reducing agents, are well known to the person skilled in the art.

The reducing agent may be any agent capable of carrying out the reduction step. Examples of suitable reagents include alkali metal borohydrides such as sodium borohydride and sodium tri(acetoxy)borohydride, of which sodium borohydride is preferred.

The solvent is not particularly restricted provided it is inert to the reaction and capable of dissolving the reactants to at least some extent. Examples of suitable solvents include water; alcohols, such as methanol, ethanol and isopropanol; ethers, such as diethyl ether and 1,2-dimethoxyethane (DME); and mixtures thereof. A mixture of water and isopropanol is preferred.

In step (c), amine (XIV) is formed by cleaving the amide (XIII), typically in the presence of acid, in a suitable solvent. Methods for carrying out the amide cleavage and suitable acids, are well known to the person skilled in the art.

The acid is not particularly restricted provided it is capable of acting as an acid. Strong acids are typically used. Examples of suitable acids include: inorganic acids such as hydrochloric acid, sulfuric acid and nitric acid, and organic acids, especially sulfonic acids such as methanesulfonic acid, trifluoromethanesulfonic acid, benzenesulfonic acid, p-toluenesulfonic acids. Hydrohalic acids are preferred and hydrochloric acid is especially preferred.

The solvent is not particularly restricted provided it is inert to the reaction and capable of dissolving the reactants to at least some extent. Examples of suitable solvents include water; alcohols, such as methanol, ethanol and isopropanol; ethers, such as diethyl ether and 1,2-dimethoxyethane (DME); and mixtures thereof. A mixture of water and isopropanol is preferred.

In step (d), the compound of formula (VII) is formed by attaching a protecting group $PG_1$ to the amine (XIV). Suitable protecting groups, and suitable reagents for their introduction, are well known to the person skilled in the art, and examples are described in "Protective Groups in Organic Synthesis", referred to above. By way of example, when $PG_1$ is Fmoc, a suitable reagent for its introduction may be N-(9H-fluoren-9-ylmethoxycarbonyloxy)succinimide.

Pharmaceutical Compositions

In an aspect of the invention, there is provided a pharmaceutical composition comprising a compound of formula (I) as described herein together with a pharmaceutically acceptable carrier. The pharmaceutical composition may be formulated for administration by any of oral, or parenteral routes. Examples of pharmaceutical carriers are well known to those skilled in the art.

Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in *Expert Opinion in Therapeutic Patents*, H (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulphate.

Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets. Vol. 1, by H. Lieberman and L. Lachman (Marcel Dekker, New York, 1980).

The compounds of the invention may also be administered parenterally, i.e. directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

Medical Uses and Methods of Treatment

In another aspect, the invention provides the compound of formula (I), or a pharmaceutically acceptable salt or solvate thereof, for use as a medicament.

In another aspect, the invention provides the compound of formula (I), or a pharmaceutically acceptable salt or solvate thereof, for use in treating a condition in a patient associated with a biological function of an $\alpha 4\beta 7$ integrin in a patient.

In another aspect, the invention provides use of the compound of formula (I), or a pharmaceutically acceptable salt or solvate thereof, in the manufacture of a medicament for treating a condition in a patient associated with a biological function of an $\alpha 4\beta 7$ integrin in a patient.

In one aspect of the invention there is provided a method for treating a condition in a patient associated with a biological function of an $\alpha 4\beta 7$ integrin, the method comprising administering to the patient a therapeutically effective amount of the compound of formula (I), or a pharmaceutically acceptable salt or solvate thereof.

In another aspect of the invention, the invention provides the compound of formula (I), or a pharmaceutically acceptable salt or solvate thereof, for use in treating inflammation or an autoimmune disease in a patient. Preferably the inflammation or autoimmune disease is gastrointestinal.

In another aspect of the invention, the invention provides use of the compound of formula (I), or a pharmaceutically acceptable salt or solvate thereof, in the manufacture of a medicament for treating inflammation or an autoimmune disease in a patient. Preferably the inflammation or autoimmune disease is gastrointestinal.

In one aspect of the invention there is provided a method of treating inflammation or an autoimmune disease in a patient, comprising administering to the patient a therapeutically effective amount of the compound of formula (I), or a pharmaceutically acceptable salt or solvate thereof. Preferably the inflammation or autoimmune disease is gastrointestinal.

In some embodiments, the condition or disease is selected from the group consisting of Inflammatory Bowel Disease (IBD), ulcerative colitis, Crohn's disease, celiac disease, microscopic colitis, collagenous colitis, eosinophilic gastroenteritis, pouchitis resulting after proctocolectomy and ileoanal anastomosis, gastrointestinal cancer, cholangitis, pericholangitis, primary sclerosing cholangitis, human immunodeficiency virus (HIV) infection in the GI tract, graft versus host disease, primary biliary sclerosis.

In preferable embodiments, the condition or disease is an inflammatory bowel disease, such as ulcerative colitis and/or Crohn's disease.

In another aspect of the invention, the invention provides the compound of formula (I), or a pharmaceutically acceptable salt or solvate thereof, for use in treating a viral disease in a patient. Preferably the inflammation or an autoimmune disease is gastrointestinal.

In another aspect of the invention, the invention provides use of the compound of formula (I), or a pharmaceutically acceptable salt or solvate thereof, in the manufacture of a medicament for treating a viral disease in a patient. Preferably the inflammation or an autoimmune disease is gastrointestinal.

In one aspect of the invention there is provided a method of treating a viral disease in a patient, comprising administering to the patient a therapeutically effective amount of the compound of formula (I), or a pharmaceutically acceptable salt or solvate thereof.

In one embodiment, the disease or condition is a local or systemic infection of a virus or retrovirus. In one embodiment, the disease or condition is HIV/AIDS. In one embodiment, the disease or condition is HIV-1. In one embodiment, the disease or condition is HIV-2.

In some embodiments, the compound of formula (I), inhibits binding of $\alpha 4\beta 7$ integrin to MAdCAM. Preferably, the compound selectively inhibits binding of $\alpha 4\beta 7$ integrin to MAdCAM.

In any embodiment, the patient is preferably a human.

As used herein, the terms "disease", "disorder", and "condition" may be used interchangeably.

As used herein, "inhibition", "treatment", "treating", and "ameliorating" are used interchangeably and refer to, e.g., stasis of symptoms, prolongation of survival, partial or full amelioration of symptoms, and partial or full eradication of a condition, disease or disorder in a subject, e.g., a mammal.

As used herein, "prevent" or "prevention" includes: (i) preventing or inhibiting the disease, injury, or condition from occurring in a subject, e.g., a mammal, in particular, when such subject is predisposed to the condition but has not yet been diagnosed as having it; or (ii) reducing the likelihood that the disease, injury, or condition will occur in the subject.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

In some embodiments, the compound is administered by a form of administration selected from the group consisting of oral, intravenous, peritoneal, intradermal, subcutaneous, intramuscular, intrathecal, inhalation, vaporization, nebulization, sublingual, buccal, parenteral, rectal, vaginal, and topical. In certain embodiments, the compound is administered subcutaneously.

Dosing

Regardless of the route of administration selected, the compounds of the present disclosure, and/or the pharmaceutical compositions of the present disclosure, may be formulated into pharmaceutically-acceptable dosage forms by conventional methods known to those skilled in the art. Actual dosage levels of the active ingredients in the pharmaceutical compositions of this disclosure may be varied so as to obtain an amount of the active ingredient which is effective to achieve the desired therapeutic response for a particular patient, composition, and mode of administration, without being unacceptably toxic to the patient.

The selected dosage level will depend upon a variety of factors including the activity of the compound of the present disclosure, or the pharmaceutically acceptable salt thereof, the route of administration, the time of administration, the rate of excretion or metabolism of the compound, the rate and extent of absorption, the duration of the treatment, other drugs, compounds and/or materials used in combination with the compound, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved. In general, a suitable daily dose of a compound of the disclosure will be that amount of the compound which is the lowest dose effective to produce a therapeutic effect. Such an effective dose will generally depend upon the factors described herein.

In some embodiments, the compound is administered as an initial dose followed by one or more subsequent doses and the minimum interval between any two doses is a period of less than 1 day, and wherein each of the doses comprises an effective amount of the compound.

In some embodiments, the effective amount of the compound is the amount sufficient to achieve at least one of the following selected from the group consisting of: a) about 50% or greater saturation of MAdCAM binding sites on α4β7 integrin molecules; b) about 50% or greater inhibition of α4β7 integrin expression on the cell surface; and c) about 50% or greater saturation of MAdCAM binding sites on α4β7 molecules and about 50% or greater inhibition of α4β7 integrin expression on the cell surface, wherein i) the saturation is maintained for a period consistent with a dosing frequency of no more than twice daily; ii) the inhibition is maintained for a period consistent with a dosing frequency of no more than twice daily; or iii) the saturation and the inhibition are each maintained for a period consistent with a dosing frequency of no more than twice daily.

In some embodiments, the compound is administered at an interval selected from the group consisting of around the clock, hourly, every four hours, once daily, twice daily, three times daily, four times daily, every other day, weekly, bi-weekly, and monthly.

In certain embodiments, the compound is administered once per day. In certain embodiments, the compound is administered once every 2 days. In certain embodiments, the compound is administered once every 3 days. In certain embodiments, the compound is administered once every 4 days. In certain embodiments, the compound is administered once every 5 days. In certain embodiments, the compound is administered once every 6 days. In certain embodiments, the compound is administered once per week. In certain embodiments, the compound is administered once every 2 weeks. In certain embodiments, the compound is administered once every 3 weeks. In certain embodiments, the compound is administered once every 4 weeks. In certain embodiments, the compound is administered once per month.

In certain embodiments, the compound is administered subcutaneously once per day. In certain embodiments, the compound is administered subcutaneously once every 2 days. In certain embodiments, the compound is administered subcutaneously once every 3 days. In certain embodiments, the compound is administered subcutaneously once every 4 days. In certain embodiments, the compound is administered subcutaneously once every 5 days. In certain embodiments, the compound is administered subcutaneously once every 6 days. In certain embodiments, the compound is administered subcutaneously once per week. In certain embodiments, the compound is administered subcutaneously once every 2 weeks. In certain embodiments, the compound is administered subcutaneously once every 3 weeks. In certain embodiments, the compound is administered subcutaneously once every 4 weeks. In certain embodiments, the compound is administered subcutaneously once per month.

In some embodiments, the compound is administered subcutaneously at a dosage of 1.4 to 5.6 µg/kg once per day. In some embodiments, the compound is administered subcutaneously at a dosage of 2.8 to 12.9 µg/kg once every 2 days. In some embodiments, the compound is administered subcutaneously at a dosage of 4.5 to 24 µg/kg once every 3 days. In some embodiments, the compound is administered subcutaneously at a dosage of 6.1 to 40 µg/kg once every 4 days. In some embodiments, the compound is administered subcutaneously at a dosage of 8.1 to 59 µg/kg once every 5 days. In some embodiments, the compound is administered subcutaneously at a dosage of 10.3 to 89 µg/kg once every 6 days. In some embodiments, the compound is administered subcutaneously at a dosage of 12.7 to 142 µg/kg once weekly.

EXAMPLES

The following Examples illustrate the preparation of compounds of the formula (I).

The Intermediates illustrate the preparation of suitable intermediates.

The following abbreviations are used:
BSA bovine serum albumin
2-CTC (2-chlorophenyl)diphenylmethyl chloride (2-chlorotrityl chloride)
DCM Dichloromethane
DIC Diisopropylcarbodiimide
DIPEA Diisopropylethylamine
DMF Dimethylformamide
DMSO Dimethylsulfoxide
Fmoc-OSu N-(9H-Fluoren-9-ylmethoxycarbonyloxy)succinimide
h, hr hour(s)
HATU 1-[Bis-(dimethylamino)methyliumyl]-1H-1,2,3-triazolo[4,5-b]pyridine-3-oxide hexafluorophosphate
HBTU [2-(1H-Benzotriazol-1-yl]-1,1,3,3-tetramethyluronium hexafluorophosphate
HFIP 1,1,1,3,3,3-Hexafluoroisopropanol
HOBT 1-Hydroxybenzotriazole
HPLC High-performance liquid chromatography
IPA 2-Propanol
LCMS Liquid chromatography mass spectrometry
MeCN Acetonitrile
MeOH Methanol
min minute(s)
Oxyma Ethyl cyanohydroxyiminoacetate
PBS Phosphate buffered saline
TRIS Tris(hydroxymethyl)aminomethane
TFA Trifluoroacetic acid
THF Tetrahydrofuran Comparative Compound 1 is Compound 1 of WO2022/002781.

Comparative Compound 2 is Compound 16 of WO2018/205008.

Synthesis of Intermediates

Intermediates 1-4

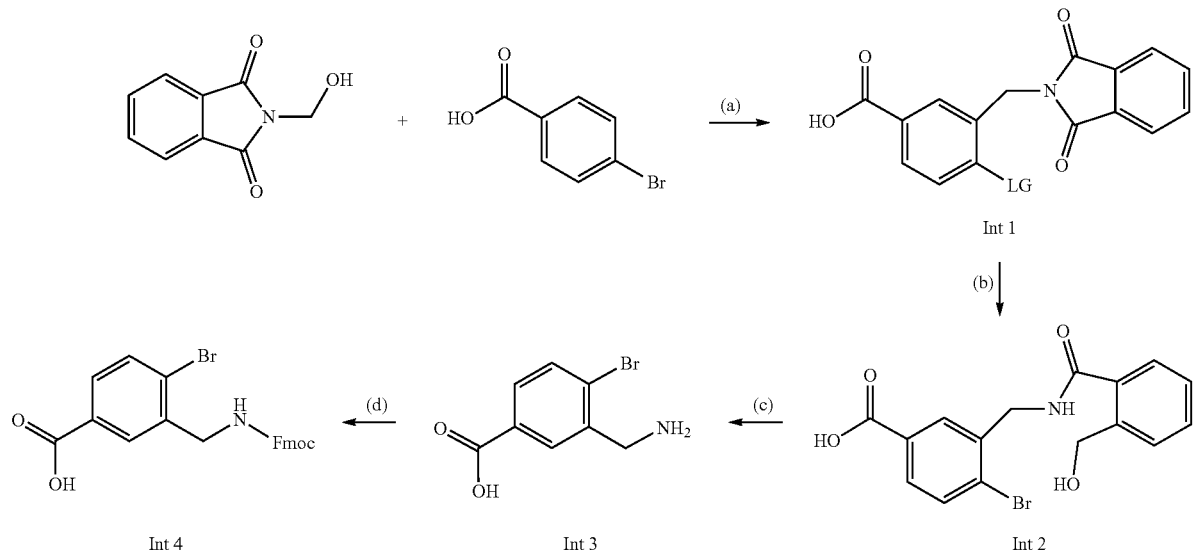

Int 4    Int 3    Int 2

Step (a)—Intermediate 1

In a 2.0 L round bottom flask equipped with a stir bar, 4-bromobenzoic acid (227 g, 1.13 mol, 1.0 eq.) was dissolved in trifluoromethanesulfonic acid (1.0 L) and cooled to 0° C. with stirring for 15 minutes. N-(Hydroxymethyl) phthalimide (200 g, 1.13 mol, 1.0 equiv.) was added in portions over 15 minutes. The resulting mixture was stirred at room temperature for 18 h. An LCMS chromatogram of the crude reaction mixture confirmed completion of reaction, as assessed by disappearance of 4-bromobenzoic acid. The mixture was poured into an ice bath (~2.5 L), with stirring. The resulting white solid was filtered and then washed with $H_2O$ until pH of the filtrate reached ~6, as assessed by wet pH paper. The resulting solid was placed under house vacuum to near-dryness to afford crude Intermediate 1.

Steps (b) and (c)—Intermediates 2 and 3

Intermediate 1 (1.13 mol, assuming 100% yield from previous step) was suspended and stirred in a 7:1 isopropanol/$H_2O$ mixture (5.0 L) in a 12.0 L round bottom flask. Solid $NaBH_4$ (214 g, 5.65 mol, 5.0 eq.) was then added, with stirring, in small portions over 4 h. The mixture was then stirred overnight at room temperature, turning slowly into a clear solution over this period. LCMS analysis confirmed complete conversion of Intermediate 1 to Intermediate 2. The reaction was quenched through gradual addition of concentrated HCl to a consistent pH value of ~1 (monitoring every 15 minutes with wet pH paper). The resulting cloudy mixture was warmed to ~70° C. for 5 h, affording a clear solution. LCMS analysis confirmed complete conversion of Intermediate 2 to the hydrochloride salt of Intermediate 3. The mixture was left to stir at room temperature overnight and the solvent was then slowly removed under a positive stream of compressed air to give crude Intermediate 3.

Step (c)—Intermediate 4

In the same 12.0 L round bottom flask from step 2, Intermediate 3 (1.13 mol, assuming 100% yield from previous step) was suspended in $H_2O$ (5.0 L). The pH of the mixture was increased to ~8, as assessed by wet pH paper, using triethylamine. A slurry of Fmoc-OSu (381 g, 1.13 mol, 1.0 eq.) in acetonitrile (500 mL) was added in one portion. The mixture was stirred at room temperature for ~65 hours and LCMS analysis confirmed complete consumption of Intermediate 3. The mixture was diluted to ~11 L with $H_2O$, acidified with concentrated HCl to pH~1, as assessed by wet pH paper, and then stirred for an additional 1.0 h. The resulting suspension was filtered and the solid filter cake washed with water (~2 L). The solid filter cake was triturated with acetonitrile (~3.5 L), filtered again and dried over house vacuum for 2 days to give Intermediate 4 (396.02 g, 0.876 mol, 77% yield over 4 steps from 4-bromobenzoic acid) as an off-white solid. This solid readily dissolved in DMF to a homogeneous solution.

Steps (a1) to (a6)—Intermediate 6

(a1) 2-CTC resin (1.5 g, 1.5 mmol/g, 2.25 mmol) was swelled with DCM (10 vol) for 15 minutes and Intermediate 5 (disclosed as Compound 4A in WO2017/079821) (1.5 eq) was added. DIPEA (4.0 eq.) in DMF (10 Vol) were added to the resin in one portion. The reaction mass was gently agitated under nitrogen bubbling for 3 hours at 25-28° C. The solvent was drained, and the resin was washed with DMF (10 vol, 3×5 min).

The resin was capped in a mixture of 10% DIPEA+20% MeOH+70% in DMF (mixture 10 Vol), at 25-28° C., for 30

Intermediates 5-9

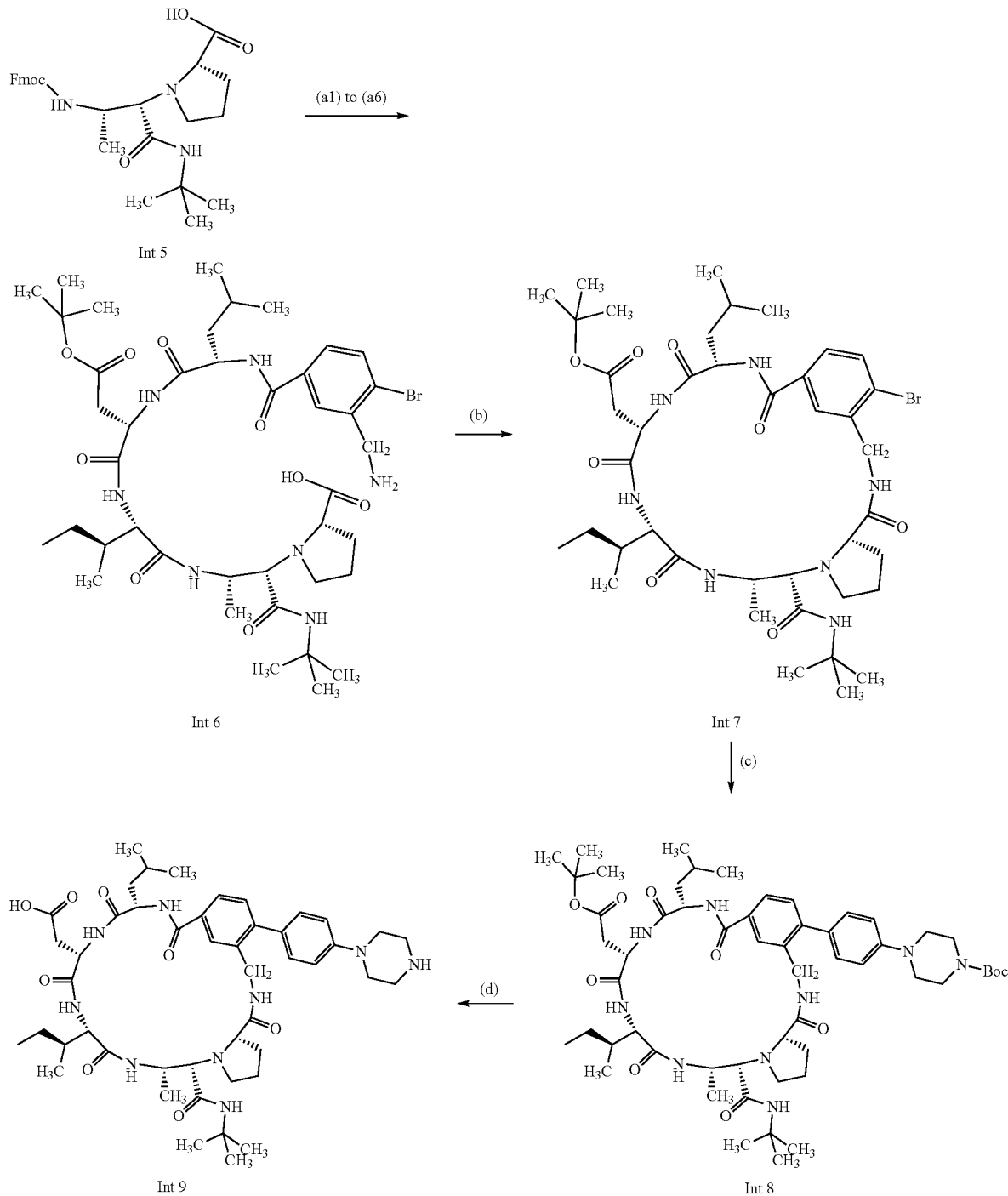

minutes. The suspension was gently agitated under nitrogen bubbling for 30 min at 25-28° C. The solvent was drained, and the resin was washed with DMF (3×10 vol, 3×5 min) and DCM (3×10 vol; 3×5 min). Deprotection: A mixture of 20% piperidine in DMF (10 vol) was added to the 2-CTC resin and gently agitated under nitrogen bubbling at 25-28° C. for 15 min. The solvents were drained. A second lot of a mixture of 20% piperidine in DMF (10 Vol) was added to the 2-CTC resin and gently agitated at 25-28° C. for 15 min. The solvents were drained. The resin was washed with DMF (10 Vol, 3×5 min) and DCM (10 Vol; 3×5 min).

After the deprotection, the resin was washed with DMF (10 vol) 5 times. (a2) Fmoc-L-Ile-OH, (1.5 eq), (a3) Fmoc-L-Asp(tBu)-OH (1.5 eq), (a4) Fmoc-L-Leu-OH (1.5 eq) and (a5) 3-(Fmoc-aminomethyl)-4-bromobenzoic acid (Intermediate 4) (1.5 eq) was coupled subsequently, each using Oxyma (1.5 eq) and DIC (2 eq) in DMF (10 vol) for 2 hours and deprotection with 20 vol % piperidine in DMF for 30 min in between. The resin was washed with DCM (3×10 vol) and dried to yield 2.3 g of peptidyl resin.

(a6) The peptidyl resin was treated with a cleavage cocktail (30 vol % HFIP/70 vol % DCM 10 vol) for 30 minutes, and then filtered. Treatment was repeated once. The combined filtrates were concentrated under reduced pressure to give crude Intermediate 6 (1.8 g). LCMS: 92% Desired compound mass: 882 (m+2H) observed at RT. HPLC: 86%

Step (b)—Intermediate 7

To a stirred solution of Intermediate 6 (1.8 g, 2.048 mmol) in DMF (40 ml, 0.05 M) was added HATU (1.12 g, 3.07 mmol) followed by DIPEA (1.13 ml, 6.1 mmol) at 25° C. The reaction mixture was stirred at 25° C. for 3 h. The reaction progress was monitored by LCMS analysis. After completion of reaction, the reaction mass was diluted with ice/water (80 ml) and extracted with ethyl acetate (3×100 ml). The separated organic layer was again washed with brine (80 ml). The separated organic layer was dried over anhydrous sodium sulfate, filtered and concentrated under reduced pressure at 35° C. to obtain Intermediate 7 as an off-white solid (0.45 g). LCMS: 58%, Desired compound mass 861 (m+H) observed HPLC: 45%

Step (c)—Intermediate 8

To a stirred (degassed for 15 min with nitrogen) solution of Intermediate 7 (300 mg, 0.344 mmol), (4-(4-tert-butoxycarbonyl)piperazino)-phenylboronic acid pinacol ester (commercially available, see also CN110862380A, Step 1: Example 228c) (134 mg, 0.344 mmol) and $K_3PO_4$ (218 mg, 1.032 mmol) in dioxane:$H_2O$ (9:1), (9 mL, 30 V) was added $Pd(PPh_3)_4$ (0.079 g, 0.0688 mmol) at 25° C. The reaction mixture was heated at 90° C. for 8 h. LCMS monitored showed conversion of starting material was completed. The mixture was diluted with water (20 ml), cooled to room temperature, filtered through a pad of Celite®, extracted with ethyl acetate (2×40 mL). The combined organic layers were dried over $Na_2SO_4$, filtered and concentrated under reduced pressure to afford crude Intermediate 8 as a pale yellow solid (300 mg). LCMS: 25%, Desired compound mass: 1046 (m+H).

Step (d)—Intermediate 9

Intermediate 8 (300 mg) was taken in a 25 ml round bottom flask and TFA:DCM (4.5 ml, 15 V) added. The reaction mixture was stirred at 25° C. for 2 h. The reaction progress was monitored by LCMS analysis. After completion of reaction, the solvent was removed under vacuum and washed with diethyl ether (3×10 ml) and dried to furnish crude product 300 mg (Off-White solid). The crude was submitted to preparative reverse phase HPLC, after purification and lyophilisation obtained weight 65 mg. LCMS: 26% Desired compound mass 888.9 (m+H).

Example 1

2,2'-((S,S,S,S,S,S,12S,8S, 11S,14S,17S,18S)-((([1,1'-biphenyl]-2,2'-dicarbonyl)bis(piperazine-4,1-diyl))bis(4,1-phenylene))bis(14-((S)-sec-butyl)-18-(tert-butylcarbamoyl)-8-isobutyl-17-methyl-2,6,9,12,15-pentaoxo-3,7,10,13,16-pentaaza-1(2,1)-pyrrolidina-5(1,3)-benzenacyclooctadecaphane-56,11-diyl))diacetic acid

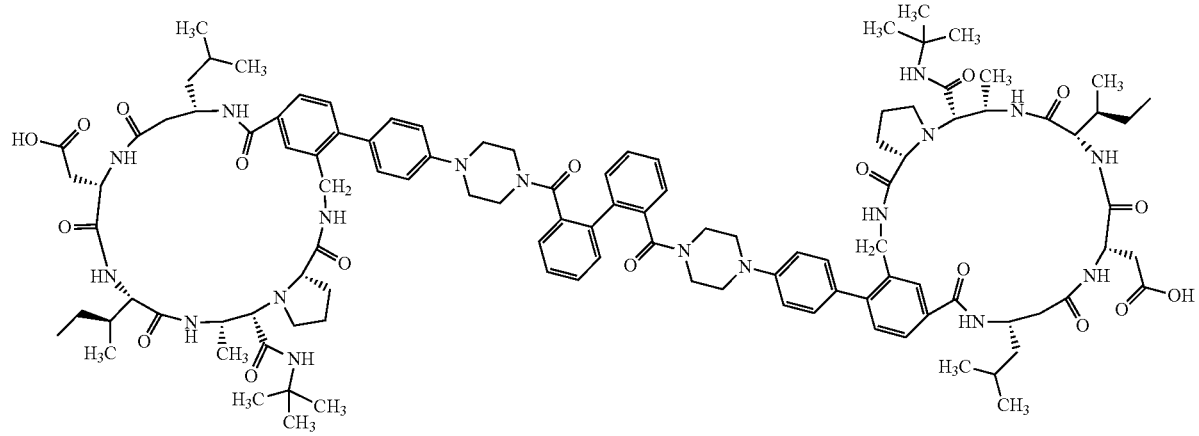 [SMILES: CC[C@H](C)[C@@H]1NC(=O)[C@H](CC(=O)O)NC(=O)C[C@H](CC(C)C)NC(=O)c2ccc(-c3ccc(N4CCN(C(=O)c5ccccc5-c5ccccc5C(=O)N5CCN(c6ccc(-c7ccc8cc7CNC(=O)[C@@H]7CCCN7[C@H](C(=O)NC(C)(C)C)[C@H](C)NC(=O)[C@H]([C@@H](C)CC)NC(=O)[C@H](CC(=O)O)NC(=O)C[C@H](CC(C)C)NC8=O)cc6)CC5)CC4)cc3)c(c2)CNC(=O)[C@@H]2CCCN2[C@H](C(=O)NC(C)(C)C)[C@H](C)NC1=O]

Intermediate 9 (40 mg, 0.045 mmol) was taken in a 25 ml round bottom flask and dry DCM (4 ml, 10 V) followed by DIPEA (0.2 ml, 1.127 mmol) added at 0° C., followed by [1,1'-biphenyl]-2,2'-dicarbonyl dichloride (prepared according to U.S. Pat. No. 4,818,771; 6.2 mg, 0.0225 mmol) in DCM was added at 0° C. dropwise. The reaction mixture was stirred at 25° C. for 3 hours. The reaction progress was monitored by LCMS analysis. After completion of reaction, the solvent was removed under vacuum and the remanens washed with diethyl ether (3×10 ml) and dried to furnish the crude product (50 mg) as an off-white solid. LCMS: 68%; Desired compound mass 992 (m/2+H).

The crude product was submitted to preparative HPLC, after purification and lyophilisation 11 mg of compound was obtained 97% pure (HPLC). The compound of Example 1 is also hereafter referred to as "compound 1".

Example 2

Testing of Compound 1 in the Integrin α4β7-MAdCAM-1 Cell Adhesion Assay

Reagents and Materials:
Recombinant human MAdCAM-1 (rhMAdCAM-1) was obtained from R&D systems (Cat #6056-MC-050).
CellTrace™ CFSE Cell Proliferation Kit, for flow cytometry was obtained from Thermo Fisher Scientific (Cat #C34554).
Peptides to be tested were aliquoted and reconstituted in-house.
Coating buffer (50 nM Sodium carbonate, pH 9.6) (Merck Millipore, Cat #S2127).
Wash buffer (PBS without $Mg^{2+}$ and $Ca^{2+}$+0.05% Tween® 20).
Binding buffer (1.5 mM $CaCl_2$, 1 mM $MnCl_2$, 100 mM NaCl, 50 mM TRIS-HCl (pH 7.5)
Blocking buffer. Stock solution is PBS (without $Mg^{2+}$ and $Ca^{2+}$)+10% BSA.
Bovine Serum Albumin (BSA) (Sigma, Cat #9430).
RPMI cell culture medium 1640 (1×)+Glutamax (Gibco Cat #61870-010).
Fetal Bovine Serum (Thermo Fisher Scientific; Cat #A4766801).
Penicillin-Streptomycin (10,000 U/mL) (Thermo Fisher Scientific; Cat #15140122).
Final growth medium: RPMI cell culture medium 1640 (1×)+Glutamax+10% FBS+1% Penicillin-Streptomycin.
Compound dilution plate (Thermo Fisher Scientific, Nunc, cat #249944).
Perkin Elmer TopSeal A plus was obtained from PerkinElmer (Cat #6050185).
Coolsink heating plate XT96F (Merck Millipore, Cat #BCS-536).
Envision 2105 Multimode plate reader (PerkinElmer, Cat #2105-0010).
F96 Maxisorp plated from Nunc was obtained from Thermo Fisher Scientific (Cat #442404).
Cells: The human B lymphocyte cell line RPMI 8866 was obtained from Merck via ECACC (European collection of authenticated cell cultures) (Cat #95041316 and lot #14G012).
Assay Protocol:
Day 0: RPMI 8866 cells were split to a concentration of 500.000 cells/mL.
A Maxisorp plate was coated with 100 μL/well of 1 μg/mL rhMAdCAM-1 in coating buffer. Plate was sealed with TopSeal A plus and incubated at 4° C. overnight.
Day 1: The plate was washed twice with 150 μL wash buffer and then blocked with 250 μL/well blocking buffer (1% BSA in PBS) for one hour at room temperature. CFSE Celltrace stock solution was prepared immediately prior to use by adding 18 μL of DMSO to one vial of CellTrace™ reagent and mixing well. Cells were pelleted by centrifugation and the supernatant was removed. Cell trace DMSO stock was diluted in pre-warmed (37° C.) PBS to a working concentration of 1 μM. Cells were gently resuspended in the PBS dye solution to a concentration of 1 million cells/mL.
The cells were incubated for 20 minutes at 37° C. and protected from light. Five times the original staining volume of culture medium were added to the cells and incubated for 5 minutes. This step removed any free dye remaining in the solution.
The cells were pelleted by centrifugation and resuspended in fresh pre-warmed complete culture medium and the cells were counted. A cell suspension with a concentration of 2 million cells/ml in binding buffer was prepared.
Compound 1 was reconstituted in DMSO to a concentration of 10 mM. Compound 1 was diluted through serial dilution to a 2×final concentration in binding buffer in a compound dilution plate.
After one hour of blocking, the Maxisorp plate was washed three times with 250 μL PBS (without $Mg^{2+}$ and $Ca^{2+}$). 50 μL test compound was added to indicated wells on the plate and 50 μL CFSE labeled cells (100,000 cells/well) was added to the wells. The plate was incubated on pre-heated coolsink plates at 37° C. and 5% $CO_2$ for 45 minutes to allow for cell adhesion.
After incubation, unbound cells were washed away. The cell plate was emptied by inverting and residues of liquid was removed by blotting on paper towel. The plate was washed two times by adding 150 μL PBS (without $Mg^{2+}$ and $Ca^{2+}$).
After the last wash, 100 μL of PBS (without $Mg^{2+}$ and $Ca^{2+}$) was added to each well and the fluorescence was read (Ex485/Em535) using a plate reader (Envision 2105 Multimode plate reader). To calculate the concentration response, the fluorescence value of control wells not containing cells was subtracted from each test well.
FIG. 1 shows the % inhibition at different concentrations of compound 1. $IC_{50}$ values were calculated using 4-parameter nonlinear fit of the data. The $IC_{50}$ value of the compound 1 is found to be $3.5\times10^{-8}$ M.

Example 3

Pharmacokinetic Characterisation of Compound 1

Method
Sprague Dawley or Wistar rats (males with a body weight of approximately 250-350 g) were given a single intravenous (i.v. bolus) injection of the peptide to be tested. Following i.v. administration of compound 1 (dose 510 nmol/kg, dosing volume 2 mg/kg), blood samples were drawn at 10 min, 15 min, 40 min, 1 h, 2 h, 4 h, 8 h, 24 h post-dose. At each sampling time point, samples from the rats were drawn by tail cut. The dosing vehicle was 20 mM phosphate buffer, 260 mM mannitol, pH 7.
Plasma samples were analyzed after protein precipitation by liquid chromatography mass spectrometry (LC-MS/MS). Individual plasma concentrations were used for calculation of the pharmacokinetic parameters using the non-compartmental approach in Phoenix WinNonlin 8.3 or a later version. Plasma terminal elimination half-life (T½) was determined as $\ln(2)/\lambda z$ where $\lambda z$ is the magnitude of the slope of the log linear regression of the log concentration versus time profile during the terminal phase. $AUC_{inf}$ is the area under the plasma concentration–time curve extrapolated to infinity ($AUC_{inf}=AUC_{last}+C_{last}/\lambda z$, where $C_{last}$ is the last observed plasma concentration). $C_0$ is the plasma concentration at the dosing time intercept and is back extrapolated by log-linear regression of the first two data points. Results for selected compounds are shown in table 1. Corresponding data for Comparative Compounds 1 and 2 are shown in Example 11 below.

TABLE 1

| Compound | Dose nmol/kg | $AUC_{inf}$ (hr*nmol/L) | $C_0$ (nmol/L) | $T_{1/2}$ (hr) |
|---|---|---|---|---|
| Compound 1 | 510 | 32200 | 90200 | 5.61 |

Example 4

Chemical Stability of Compound 1 and Comparative Compound 1

In this Example, the stability of Compound 1 was tested and compared with that of Comparative Compound 1.
Materials and Method The chemical stability of the compounds was tested under aqueous conditions at 1 mg/mL in 20 mM phosphate pH 7, 20 mM phosphate pH 8 and 20 mM glycine pH 9. Chemical stability was followed for the duration of two weeks at 40° C., using the normalized endpoint purity to assess chemical stability.

HPLC for Chemical Purity Determination

The formulated samples were measured on T=0, 1 and 2 weeks by reverse phase HPLC using a conventional HPLC apparatus, such as a Dionex® Ultimate 3000 system, for binary gradient application equipped with a column, such as 1.5×150 mm Acquity UPLC peptide CSH column, and using a suitable gradient from buffer A (0.3% trifluoroacetic acid, aq.) and buffer B (0.3% trifluoroacetic acid, 90% MeCN, aq.), with a column temperature of 50° C. and a gradient from 20 to 80% MeCN over 19 minutes. Purity is determined as peak area.

Chemical Stability of Compound 1 and Comparative Compound 1
Stock Solutions

The compound was carefully weighed out and dissolved in MQ water to 2 mg/mL and pH adjusted to neutral pH (pH 6-8). The stock solution was equilibrated 15 minutes at ambient temperature, at which point no visible particles were present. 40 mM buffer stock solutions were prepared for each pH condition tested.

Chemical Stability Assay:

The formulations for chemical testing were made by mixing peptide stock and buffer stock in a ratio of 1:1. This was done for each buffer/pH condition in Protein LoBind tube 2.0 mL (Eppendorf). These samples were placed in a temperature-controlled chamber set to 40° C. for two weeks.

Figure 2:
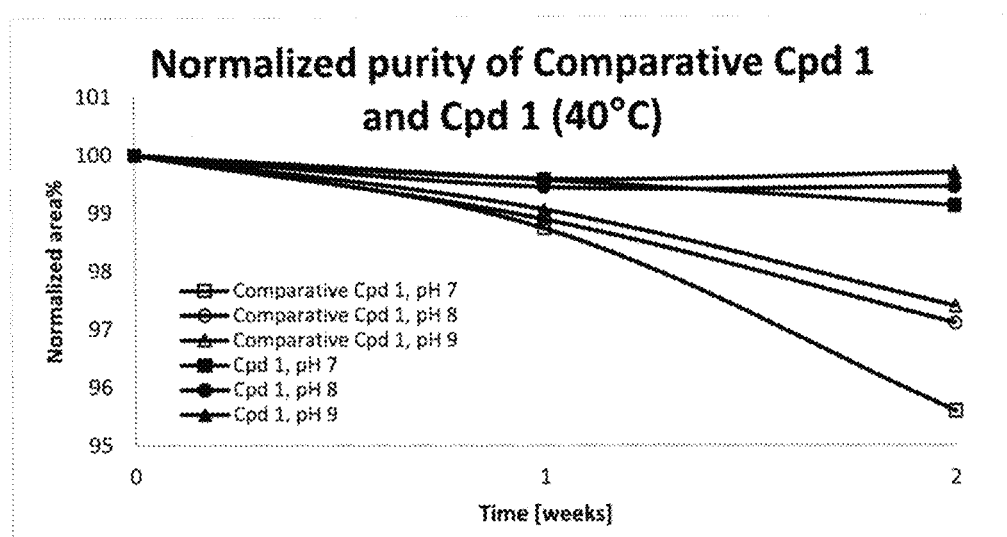
FIG. 2 shows the normalised purity values for compound 1 and comparative compound 1 over two weeks' storage at 40° C., as determined by the method described in Example 4.

Measuring Chemical Stability:

Chemical stability was assessed by taking out a small volume and running on the Dionex® Ultimate 3000 system. The generated chromatograms were integrated and normalized purity data generated by normalization against the freshly dissolved sample (T=0). The endpoint data after 2 weeks storage at 40° C. are reported below in Table 2 and shown in FIG. 2.

TABLE 2

| Compound | Formulation | Normalized purity after two weeks storage at 40° C. |
|---|---|---|
| Comparative Compound 1 | 20 mM phosphate pH 7 | 95.6 |
| Comparative Compound 1 | 20 mM phosphate pH 8 | 97.1 |
| Comparative Compound 1 | 20 mM glycine pH 9 | 97.4 |
| Compound 1 | 20 mM phosphate pH 7 | 99.1 |
| Compound 1 | 20 mM phosphate pH 8 | 99.4 |
| Compound 1 | 20 mM glycine pH 9 | 99.7 |

Example 5

Further Pharmacokinetic Characterisation of Compound 1

Method

Beagle dogs (males with a body weight of approximately 10-12 kg) were given a single subcutaneous (s.c.) and intravenous (i.v.) injection of the peptides to be tested.

Following s.c. and i.v. administration of the selected compounds (dose 200 µg/kg), dosing volume 0.1 ml/kg, blood samples were drawn at 0, 30 min, 1 h, 2 h, 4 h, 8 h, 24 h, 48 h, 72 h and 144 h post-dose for Comparative Compound 1 and 0, 30 min, 1 h, 2 h, 4 h, 8 h, 24 h, 48 h, 72 h, 96 h and 168 h for Compound 1.

Blood was sampled through a venflon on day 1 (excluding the 8-hour timepoint). At the 8-hour sampling time, and the sampling timepoints hereafter, the blood was be sampled through v. jugularis with a vacutainer and vacutainer needle. The dosing vehicle was PBS buffer, pH 7.

Plasma samples were analyzed after protein precipitation by liquid chromatography mass spectrometry (LC-MS/MS). Individual plasma concentrations were used for calculation of the pharmacokinetic parameters using the non-compartmental approach in Phoenix WinNonlin 8.3 or a later version. Plasma terminal elimination half-life (T½) was determined as $\ln(2)/\lambda z$ where $\lambda z$ is the magnitude of the slope of the log linear regression of the log concentration versus time profile during the terminal phase. $AUC_{inf}$ is the area under the plasma concentration–time curve extrapolated to infinity ($AUC_{inf}=AUC_{last}+C_{last}/\lambda z$, where $C_{last}$ is the last observed plasma concentration). $C_0$ is back extrapolated by log-linear regression of the first two data points. Results for selected compounds are shown in Table 3.

TABLE 3

| Compound No. | Admin Route | $t_{1/2}$ (hr) | $C_{max}$ (nmol/L) | $AUC_{inf}$ (hr*nmol/L) |
|---|---|---|---|---|
| Comparative Compound 1 | IV | 23.5 | 625 | 3780 |
| Comparative Compound 1 | SC | 26.6 | 137 | 3060 |
| Compound 1 | IV | 53.0 | 743 | 19300 |
| Compound 1 | SC | 95.2 | 127 | 21800 |

As can be seen from Table 3, Compound 1 exhibits a marked increase in t½ and higher AUC compared with Comparative Compound 1. This increase is surprising considering the small structural differences between the compounds.

Example 6

Further Pharmacokinetic Characterisation of Compound 1

Method

Beagle dogs (males with a body weight of approximately 10-12 kg) were given a single subcutaneous (s.c.) injection of the peptides to be tested. Following s.c. administration of the selected compounds (dose 10, 20, 50, 100, 200 and 400 µg/kg), dosing volume 0.1 m/kg, blood samples were drawn at 0, 3, 6, 8, 12, 24, 48, 72, 96, 120, 144, 168, 192, 216, 240, 264, 288, 312, 336, 576, 744, 936, 1104 and 1272 hours.

Blood was sampled through a venflon on day 1 (excluding the 8-hour timepoint). At the 8-hour sampling time, and the sampling timepoints hereafter, the blood was be sampled through v. jugularis with a vacutainer and vacutainer needle. The dosing vehicle was PBS buffer, pH 7.

Plasma samples were analyzed after protein precipitation by liquid chromatography mass spectrometry (LC-MS/MS). Individual plasma concentrations were used for calculation of the pharmacokinetic parameters using the non-compartmental approach in Phoenix WinNonlin 8.3 or a later version. Plasma terminal elimination half-life (T½) was determined as $\ln(2)/\lambda z$ where $\lambda z$ is the magnitude of the slope of the log linear regression of the log concentration versus time profile during the terminal phase. $AUC_{inf}$ is the area under the plasma concentration–time curve extrapolated to infinity ($AUC_{inf}=AUC_{last}+C_{last}/\lambda z$, where $C_{last}$ is the last observed plasma concentration). $C_0$ is back extrapolated by log-linear regression of the first two data points. Results for selected compounds are shown in Table 4.

TABLE 4

| Cpd. No. | Admin Route | Dose (µg/kg) | t½ (hr) | $T_{max}$ (hr) | $C_{max}$ (nmol/L) | $AUC_{inf}$ (hr*nmol/L) |
|---|---|---|---|---|---|---|
| Cpd 1 | SC | 10 | 340 | 20 | 18.1 | 2460 |
| | | 20 | 460 | 20 | 43.1 | 5680 |
| | | 50 | 340 | 20 | 102 | 11600 |
| | | 100 | 230 | 20 | 504 | 58600 |
| | | 200 | 230 | 20 | 417 | 72500 |
| | | 400 | 260 | 20 | 927 | 158000 |

The data presented in Table 4 supplement those in Table 3 in showing that the t½ exhibited by Compound 1 is surprisingly long following subcutaneous administration. This is surprising considering its molecular structure and the comparatively lower t½ displayed by Comparative Compound 1 in the results shown in Table 3.

Example 7

Testing of Compounds in the Integrin α4β7-MAdCAM Cell Adhesion Assay and the Integrin α4β1-VCAM-1 Cell Adhesion Assay Recombinant human MAdCAM-1 (rhMAdCAM-1) was obtained from R&D systems (Cat #6056-MC-050).

Recombinant human VCAM-1 (rhVCAM-1) was obtained from R&D systems (Cat 862-VC-100).

CellTrace™ CFSE Cell Proliferation Kit, for flow cytometry was obtained from Thermo Fisher Scientific (Cat #C34554).

Peptides to be tested were aliquoted and reconstituted in-house.

Coating buffer (50 nM Sodium carbonate, pH 9.6) (Merck Millipore, Cat #S2127).

Wash buffer (PBS without $Mg^{2+}$ and $Ca^{2+}$+0.05% Tween® 20).

DMEM Binding buffer (Dulbecco Modified Eagle Medium, Phenol red free (DMEM) (Gibco Cat #31053-028), 1 mM $MnCl_2$ (Sigma Aldrich, Cat #M1787-10×1 ML), 20 mM HEPES (pH 7.5) (Gibco cat #15630-056), 1 mM Sodium Pyruvate (Gibco cat #11360-039), 0.05% Casein (Sigma Aldrich, Cat #C4765))

Blocking buffer: Stock solution is PBS (without $Mg^{2+}$ and $Ca^{2+}$)+10% BSA.

Bovine Serum Albumin (BSA) (Sigma, Cat #9430).

RPMI cell culture medium 1640 (1×)+Glutamax (Gibco Cat #61870-010).

Fetal Bovine Serum (Thermo Fisher Scientific; Cat #A4766801).

Penicillin-Streptomycin (10,000 U/mL) (Thermo Fisher Scientific; Cat #15140122).

Final growth medium: RPMI cell culture medium 1640 (1×)+Glutamax+10% FBS+1% Penicillin-Streptomycin.

Compound dilution plate (Thermo Fisher Scientific, Nunc, cat #249944).

Perkin Elmer TopSeal A plus was obtained from PerkinElmer (Cat #6050185).

Coolsink heating plate XT96F (Merck Millipore, Cat #BCS-536).

Envision 2105 Multimode plate reader (PerkinElmer, Cat #2105-0010).

F96 Maxisorp plated from Nunc was obtained from Thermo Fisher Scientific (Cat #442404).

Cells: The human B lymphocyte cell line RPMI 8866 was obtained from Merck via ECACC (European collection of authenticated cell cultures) (Cat #95041316 and lot #14G012). The human B lymphocyte cell line RAMOS was obtained from the Zealand Pharma culture collection.

Assay Protocol:

Day 0: RPMI 8866 and RAMOS cells were split to a concentration of 500,000 cells/mL.

A Maxisorp plate was coated with 100 µL/well of 1 µg/mL rhMAdCAM-1 in coating buffer and a second Maxisorp plate was coated with 100 µL/well of 1 µg/mL rhVCAM-1 in coating buffer. The plates were sealed with TopSeal A plus and incubated at 4° C. overnight.

Day 1: The plates were washed twice with 150 µL wash buffer and then blocked with 250 µL/well blocking buffer (1% BSA in PBS) for one hour at room temperature. CFSE Celltrace stock solution was prepared immediately prior to use by adding 18 µL of DMSO to one vial of CellTrace™ reagent and mixing well. Cells were pelleted by centrifugation and the supernatant was removed. Cell trace DMSO stock was diluted in pre-warmed (37° C.) PBS to a working concentration of 1 µM. Cells were gently resuspended in the PBS dye solution to a concentration of 1 million cells/mL.

The cells were incubated for 20 minutes at 37° C. and protected from light. Five times the original staining volume of culture medium were added to the cells and incubated for 5 minutes. This step removed any free dye remaining in the solution.

The cells were pelleted by centrifugation and resuspended in fresh pre-warmed complete culture medium and the cells were counted. A cell suspension with a concentration of 2 million cells/ml in DMEM binding buffer was prepared.

Compound 1 and Comparative compounds 1 and 2 were reconstituted in DMSO to a concentration of 10 mM. All compounds were diluted through serial dilution to a 2×final concentration in DMEM binding buffer in a compound dilution plate.

After one hour of blocking, the Maxisorp plates were washed three times with 250 μL PBS (without $Mg^{2+}$ and $Ca^{2+}$). 50 μL test compounds were added to indicated wells on the plate and 50 μL CFSE labeled cells (100,000 cells/well) was added to the wells. CFSE-labelled RPMI 8866 cells were added to the plate coated with rhMAdCAM-1 and CFSE-labelled RAMOS cells were added to the plate coated with rhVCAM-1. The plates were incubated on preheated coolsink plates at 37° C. and 5% $CO_2$ for 45 minutes to allow for cell adhesion.

After incubation, unbound cells were washed away. The cell plates were emptied by inverting and residues of liquid were removed by blotting on paper towel. The plates were washed two times by adding 150 μL PBS (without $Mg^{2+}$ and $Ca^{2+}$).

After the last wash, 100 μL of PBS (without $Mg^{2+}$ and $Ca^{2+}$) was added to each well and the fluorescence was read (Ex485/Em535) using a plate reader (Envision 2105 Multimode plate reader). To calculate the concentration response, the fluorescence value of control wells not containing cells was subtracted from each test well. IC50 values were calculated using 4-parameter nonlinear fit of the data.

Table 5 shows the $IC_{50}$ values of compound 1 and comparative compounds on both α4β7 and α4β1.

TABLE 5

| Compound No. | a4p7 RPMI8866/ MAdCAM-1 adhesion $IC_{50}$ (nM) | a4p1 RAMOS/ VCAM-1 adhesion $IC_{50}$ (nM) | Selectivity ratio |
| --- | --- | --- | --- |
| Compound 1 | 7.2 | 115 | 16.0 |
| Comparative compound 1 | 26.6 | 304 | 11.4 |
| Comparative compound 2 | 7.5 | 122 | 16.3 |

Example 8

Testing of Compound 1 in the Mouse Dextran Sodium Sulfate (DSS) Colitis Model

The current study was conducted in the mice model of Dextran Sodium Sulfate (DSS) induced ulcerative colitis (UC). DSS induces chronic colitis in experimental animals when given orally in drinking water for 6 days followed by no DSS in drinking water for 6 days. Chronic intestinal inflammation is associated with body weight loss, diarrhea, blood in the stool and the infiltration of leucocytes from the blood to intestinal tissue. Among those cells, subpopulations of T lymphocytes such as Th1 and Th17 play an important role in the initiation and chronicity of inflammation. Trafficking of T cells from blood to target tissue is a complex process that is controlled by molecularly distinct adhesion and signaling steps. As such, the a4b7 and MAdCAM-1 adhesion mechanism may be closely involved in lymphocyte trafficking to the site of inflammation in the gut.

Evaluation of the therapeutic potential of cpd 1 in a mice model of dextran Sodium Sulfate (DSS) induced ulcerative colitis (UC) was undertaken Animals Male C57Bl/6 mice (Charles River, Germany), weighing 20-25 g at arrival and 8 weeks of age were used for this study. Following arrival to the animal facility, all animals were subjected to a general health evaluation. An acclimation period of 5 days was allowed before the beginning of the study.

Animal Care Committee

The study was conducted at CRO Selvita, Zagreb, Croatia in their Association for Assessment and Accreditation of Laboratory Animal Care (AALAC) accredited animal facility. All animal-related research was conducted in accordance with 2010/63/EU and National legislation regulating the use of laboratory animals in scientific research and for other purposes (Official Gazette 55/13). An Institutional Committee on Animal Research Ethics (CARE-Zg) oversees that animal-related procedures are not compromising the animal welfare.

Housing Environment

The animals were housed under standardized environmental conditions. The mice were housed in cages with solid floors (TECNIPLAST cages, type III, polysulfonate material, surface 425 mm×266 mm×185 mm). Ten animals were housed per cage on irradiated, corn cob grits-dust-free bedding for laboratory animals (Scobis Due—Mucedola, Italy) with a provision of one cotton nestlet for nest making, a Des Res paper shelter (Lillico Serving Biotechnology, UK) and Wood Gnawing Blocks (Certified, Bio-Serv USA). Each cage was equipped with a manual water distribution system. A standard certified commercial rodent diet was provided ad libitum. Tap water was provided ad libitum. It is considered that there are no known contaminants in the diet and water that would interfere with the objectives of the study. Each cage was identified for the corresponding group, indicating the treatment and the identity of the animals housed in the cage. Mice from different treatment groups were not mixed. The animal room was maintained at a controlled temperature of 22±2° C. and a relative humidity of 55±10%. A controlled lighting system assured 12 hours light; 12 hours dark per day to the animals. Adequate ventilation of 15-20 air changes per hour was maintained.

Induction of Ulcerative Colitis in C57Bl/6 Mice

Experimental UC was induced in mice by the administration of 1.5% (w/v) Dextran sulfate sodium (DSS) salt reagent grade: MP Biomedicals, cat. no. 160110 (36-50 kDa) in their drinking water for 6 days. On day 7, DSS drinking water was replaced with regular water until the end of the study at day 12. Group 1 (see table 6) did not receive DSS in the drinking water and served as a control for a healthy colon.

TABLE 6

| Group | Number of animals/ group | DSS in drinking water (DO-D6) Water only(D6-D12) | Treatment D-2-D11 | Dose concentration/dose occation and dosing frequency |
| --- | --- | --- | --- | --- |
| 1 | 5 | Water | Vehicle | 10 mL/kg (D-2 and D-1 PO/TID) (D0-D11 PO/BID) |
| 2 | 10 | 1.5% | Vehicle | 10 mL/kg (D-2 and D-1 PO/TID) (D0-D11 PO/BID) |
| 3 | 10 | DSS | Compound 1 10000 nmol/kg | 10000 nmol/kg (20 mg/kg) (D-2 and D-1 PO/TID) (D0-D11 PO/BID) |

TABLE 6-continued

| Group | Number of animals/ group | DSS in drinking water (D0-D6) Water only(D6-D12) | Treatment D-2-D11 | Dose concentration/dose occation and dosing frequency |
|---|---|---|---|---|
| 4 | 10 | | Compound 1 1250 nmol/kg | 1250 nmol/kg (2.5 mg/kg) (D-2 and D-1 PO/TID) (D0-D11 PO/BID) |

PO = per os; TID = three times daily; BID = two times daily

The studied test article and the vehicle were dosed orally at 10 mL/kg. Dosing volume was individually adjusted according to the body weight of each animal to reach the target dose indicated for the individual groups.

Preparation of Test Compound and Vehicle

TABLE 7

| Test substance | Solution |
|---|---|
| Vehicle | 0.5% HPMC with 20 mM phosphate pH 7.5 |
| compound 1 | 2 mg/mL or 0.25 mg/ml in 0.5% hydroxy propyl methyl cellulose (HPMC) with 20 mM phosphate pH 7.5 |

The vehicle was prepared once for the entire study and stored at +4° C.

The dosing solutions were made in the afternoon for the next day's dosing events and were stored at +4° C. and dosed to the animals at room temperature.

Vehicle and compound 1 were dosed TID on day −2 and day −1 and thereafter BID.

Disease Activity Index (DAI) Assessment

To assess the severity of colitis, the disease activity index (DAI) was calculated as a combined score of a) weight loss b) stool consistency and c) colorectal bleeding daily with maximum score of 12. The baseline DAI score was determined on day −2.

Animals were weighed daily starting on day −2 prior to first DSS challenge and % of body weight change was calculated using the formula: [(Weight on day X−Initial weight)/Initial weight]×100. Body weight change expressed as one-digit value (X %) was used to determine weight loss score as described in Table 8.

Samples of stool was collected daily during handling of animals. Each stool pellet was placed into a 2 mL U-bottom Eppendorf tube filled with 1.0 mL of water and vortexed at max speed for 3-5 sec. For stool consistency, 0 points was assigned for well-formed pellets, 1 point was assigned to semi-formed pellets, 2 points for pasty pellets (loose stool), 3 points for not completely liquid stools (mild diarrhea) and 4 points for liquid stools (gross diarrhea).

Colorectal bleeding score was defined with 0 for no presence of blood in stool or anal region, 2 for visible blood in stool pellets and 4 for gross bleeding and/or blood around anus region. Each score will be determined as indicated in Table 8.

TABLE 8

Disease activity index (DAI) for DSS-Treated Animals*

| Weight loss (%) | Score | Stool consistency | Score | Colorectal bleeding | Score |
|---|---|---|---|---|---|
| <1% | 0 | Formed and hard | 0 | Absence | 0 |
| 1-5% | 1 | Formed and soft | 1 | | |
| 5.1-10% | 2 | Loose stool | 2 | Presence | 2 |
| 10.1-15% | 3 | Mild diarrhoea (watery) | 3 | | |
| >15.1% | 4 | Gross diarrhoea | 4 | Gross | 4 |

*Table adapted from Current protocols in Pharmacology 72:5.58 (Bang, B. and Lichtenberger, L.M. 2016. Methods of inducing inflammatory bowel disease in mice. Curr. Protoc. Pharmacol. 72:5.58.1-5.58.42.doi: 10.1002/0471141755.ph0558s47.)

Colon Weight and Length Measurements and Collection of Colon Samples for Histopathology Once the mouse was euthanized at termination of the study, the colon was removed including the cecum. Colon length was measured by ruler from cecum to anus, excluding the cecum length. Next the colon was flushed with cold PBS and weighed, and its length was measured. Colon length in centimeter (cm) was measured by ruler from cecum to anus, excluding the cecum length. The colon was subsequently flushed with cold PBS, weighed, and cut in three segments. Segment 1 (proximal part) and segment 3 (distal part) was fixed in 10% formalin for histologic analysis.

Colon Preparation and Histology Analysis

The excised colon was divided into proximal and distal segment, cut and paraffin-embedded in toto (two blocks).

Histological analysis was performed on PAS-stained slides using the score published by Nishitani et al. (*Int Immunopharmacol.* 2009, 9, 1444-51) as outlined in table 9 below:

TABLE 9

| | Severity of inflammation | Layers involved | Epithelial damage score | Extent |
|---|---|---|---|---|
| 0 | No inflammation | No inflammation | Intact epithelium | No lesions |
| 1 | Mild | Mucosa | Disruption of architecture | Punctuate |
| 2 | Moderate | Mucosa and submucosa | Erosion | Multifocal |
| 3 | Severe | Transmural | Ulceration | Diffuse |

Results

Figure 3:
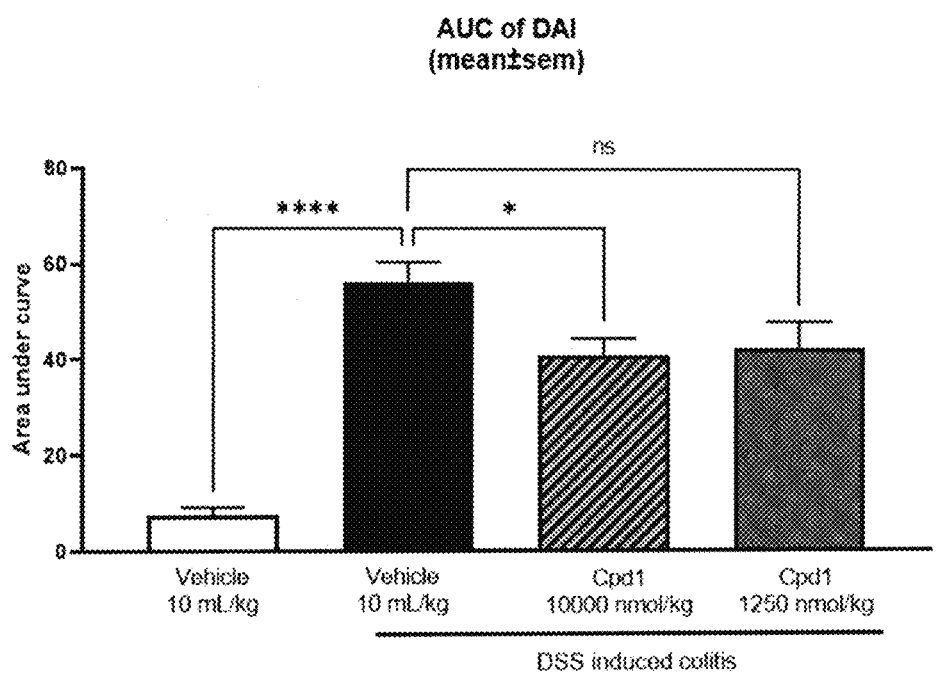
FIG. 3 shows a histogram plot of the area under curve (AUC) disease activity index (DAI) score expressed as mean±SEM for each group for compound 1 when tested in the DSS mouse colitis model according to example 8. The dose concentration of compound 1 is the p.o. dose administered per dose occasion. Statistical differences among groups were determined using a one-way ANOVA, followed by Dunnett's multiple comparisons test, to compare each group to the DSS+vehicle group (black in histogram). *$p<0.05$; ns=not significant.

The DAI score was assessed individually based on the severity of three specific symptoms: blood in stool, stool consistency and body weight loss. The area under curve (AUC) for each group was calculated (FIG. 3). The DAI score AUC increased following the administration of DSS in drinking water in the DSS treated groups (DSS+vehicle; DSS+compound 1 10000 nmol/kg and DSS+compound 1 1250 nmol/kg). The DAI score AUC was significantly increased in the DSS vehicle group compared to the vehicle control (no DSS) group. The administration of the highest dose of compound 1 (10000 nmol/kg) from day −2 resulted in a significant reduction in DAI score AUC compared with the DSS+vehicle group (FIG. 3).

Figure 4:
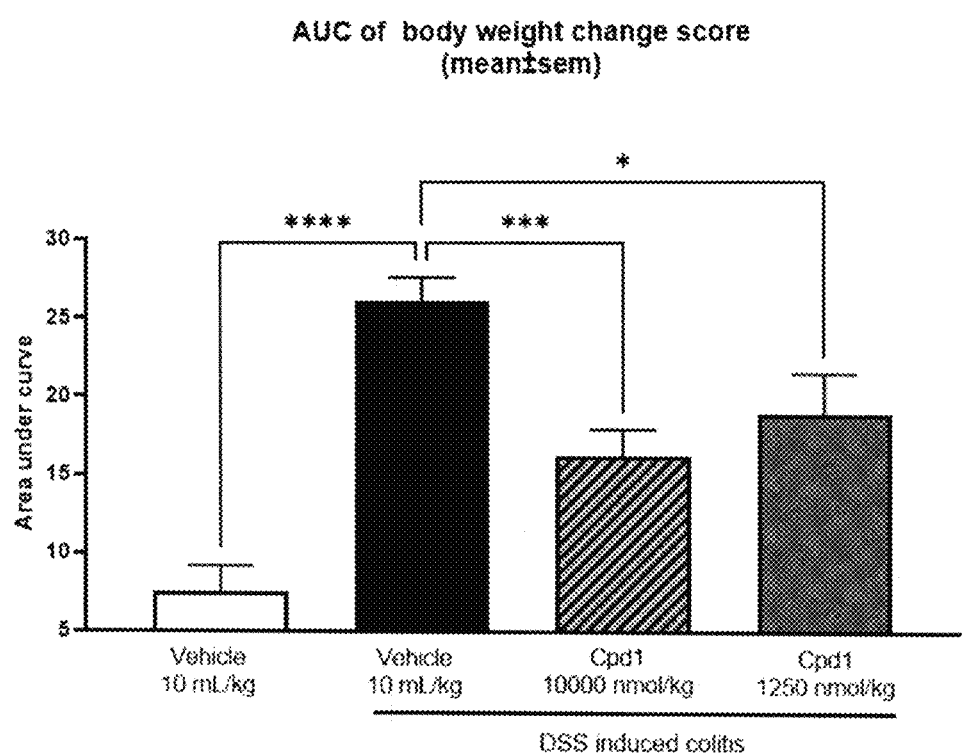
FIG. 4 shows a histogram plot of the area under curve (AUC) body weight change score expressed as mean±SEM for each group for compound 1 when tested in the DSS mouse colitis model according to example 8. The dose concentration of compound 1 is the p.o. dose administered per dose occasion. Statistical differences among groups were determined using a one-way ANOVA, followed by Dunnett's multiple comparisons test, to compare each group to the DSS+vehicle group (black in histogram). *p<0.05; ns=not significant.

A key disease severity measure in the DSS colitis model is body weight loss, therefore weight gain is a good indicator of therapeutic effect of a test compound. The body weight change score is included in the disease activity index (DAI) score (see table 8). The body weight change score AUC for each group was calculated (FIG. 4). The body weight change score AUC increased following the administration of DSS in drinking water in the DSS treated groups (DSS+vehicle; DSS+compound 1 10000 nmol/kg and DSS+compound 1 1250 nmol/kg). The body weight change score AUC was significantly increased in the DSS vehicle group compared to the vehicle control (no DSS) group. A significant therapeutic effect resulting in a significant reduction in body weight change score AUC was observed following administration of compound 1 (10000 nmol/kg) and compound 1 (1250 nmol/kg) from day −2 compared with the DSS+vehicle group (FIG. 4).

Figure 5:
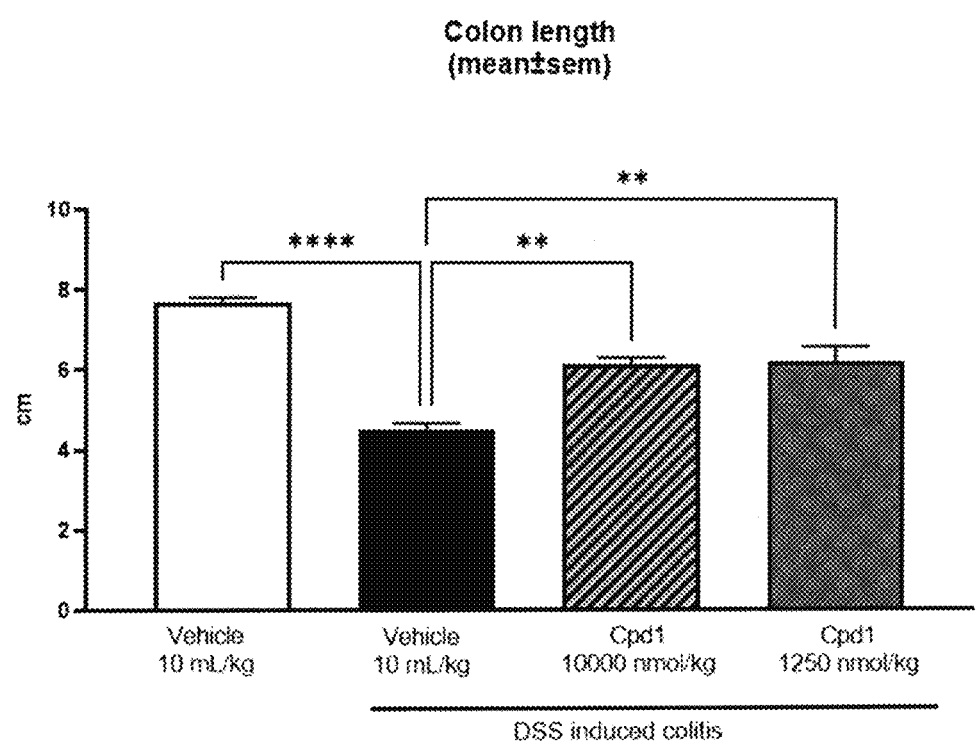
FIG. 5 shows a histogram plot colon length (cm) expressed as mean±SEM for each group for compound 1 when tested in the DSS mouse colitis model according to example 8. The dose concentration of compound 1 is the p.o. dose administered per dose occasion. Statistical differences among groups were determined using a one-way ANOVA, followed by Dunnett's multiple comparisons test, to compare each group to the DSS+vehicle group (black in histogram). *p<0.05; ns=not significant.

Colon shortening is a key macroscopic change that correlates with disease severity in DSS colitis and therefore colon length is often investigated as part of termination procedures by measurement of the colon length in centimeter (cm). The colon length (cm) was measured for all animals in the experiment (FIG. 5). As shown in FIG. 5, the colon length is shortened following the administration of DSS in drinking water in the DSS treated groups (DSS+vehicle; DSS+compound 1 10000 nmol/kg and DSS+compound 1 1250 nmol/kg). The colon length was significantly reduced in the DSS+vehicle group compared to the vehicle control (no DSS) group. The administration of the high dose of compound 1 (10000 nmol/kg) and the low dose of compound 1 (1250 nmol/kg) from day −2 resulted in a significantly increased colon length compared with the DSS vehicle group (FIG. 5).

Figure 6:
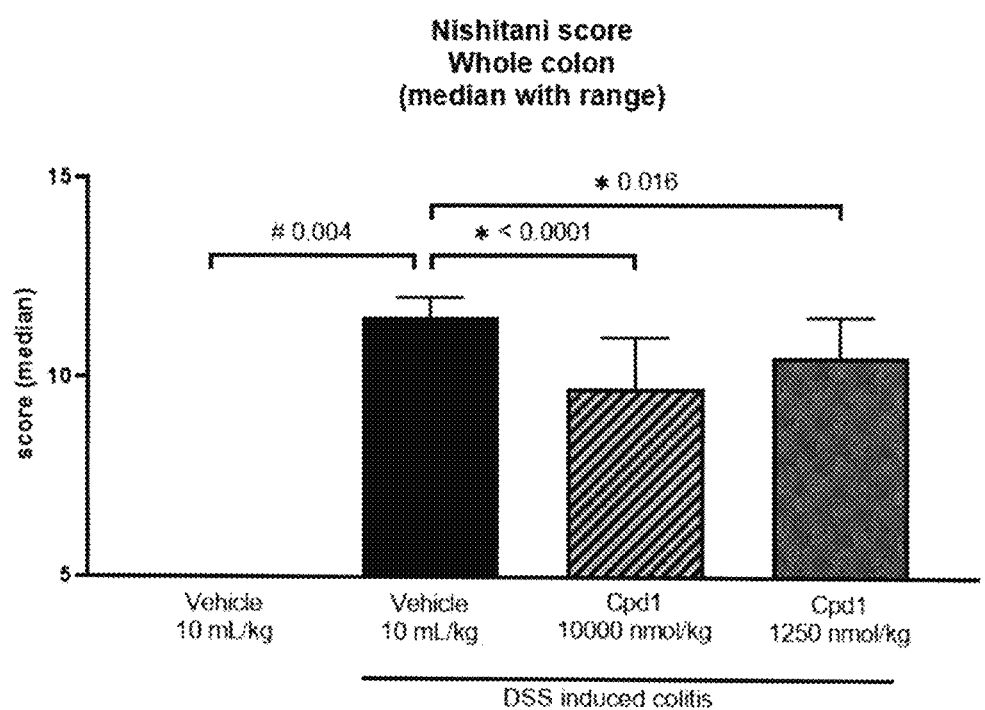
FIG. 6 shows a histogram plot histological analysis of whole colon by use of the Nishitani sum score expressed as median with ranges for each group for compound 1 when tested in the DSS mouse colitis model according to example 8. The dose concentration of compound 1 is the p.o. dose administered per dose occasion. Statistical differences among groups were determined using a one-way ANOVA, followed by Dunnett's multiple comparisons test, to compare each group to the DSS+vehicle group (black in histogram). *p<0.05; ns=not significant. For comparison between the DSS+vehicle group versus the vehicle (no DSS) control group, a Wilcoxon signed rank test was used; #=p<0.05.

A histological analysis of the colon is a means to evaluate disease severity and inflammation in the DSS induced colitis model. A histological analysis was conducted on the colon of individual mice by using the Nishitani sum score as described in table 9. The sum Nishitani score on whole colon (proximal and distal colon) score for each group is shown in FIG. 6. The whole colon Nishitani sum score increased following the administration of DSS in drinking water in the DSS treated groups (DSS+vehicle; DSS+compound 1 10000 nmol/kg and DSS+compound 1 1250 nmol/kg). The Nishitani sum score was significantly increased in the DSS+vehicle group compared to the vehicle control (no DSS) group. Administration of the high dose of compound 1 (10000 nmol/kg) and the low dose of compound 1 (1250 nmol/kg) from day −2 resulted in a significantly reduced whole colon Nishitani sum score compared with the DSS+vehicle group (FIG. 6).

Figure 7:
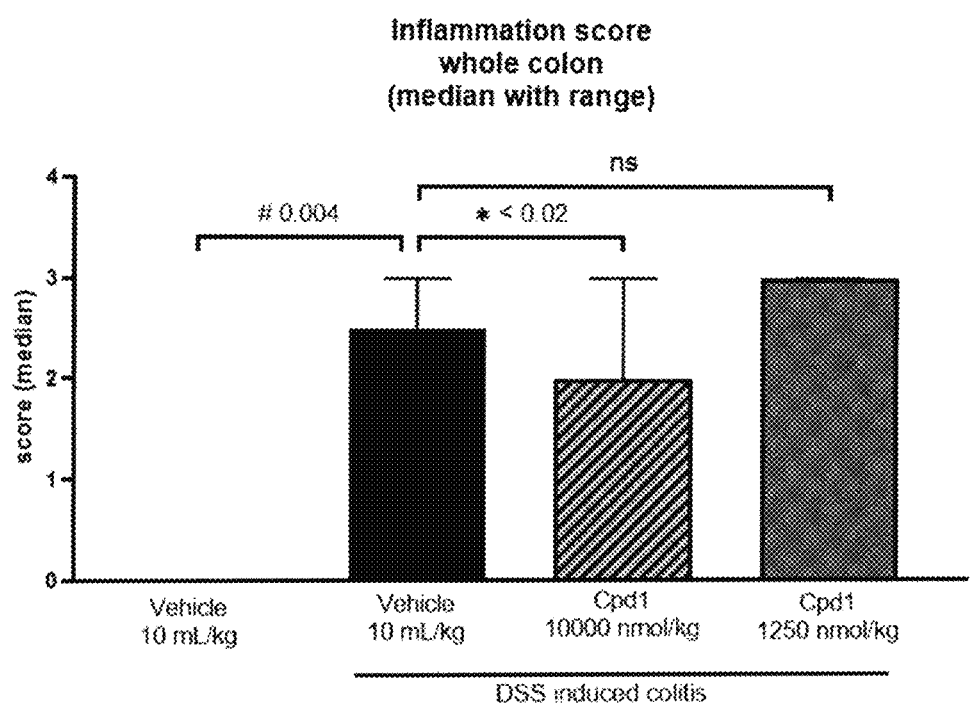
FIG. 7 shows a histogram plot histological analysis of whole colon inflammation severity score expressed as median with ranges for each group for compound 1 when tested in the DSS mouse colitis model according to example 8. The dose concentration of compound 1 is the p.o. dose administered per dose occasion. Statistical differences among groups were determined using a non-parametric Mann-Whitney test, to compare each group to the DSS+ vehicle group (black in histogram). *p<0.05; ns=not significant. For comparison between the DSS+vehicle group versus the vehicle (no DSS) control group, a Wilcoxon signed rank test was used; #=p<0.05.

Histological evaluation of inflammation severity is part of the Nishitani sum score assessment of disease manifestations in the colon induced by DSS. The inflammation severity score on whole colon (proximal and distal colon) score for each group in shown in FIG. 7. The histological inflammation severity score increased following administration of DSS in drinking water in the DSS treated groups (DSS+vehicle; DSS+compound 1 10000 nmol/kg and DSS+compound 1 1250 nmol/kg). The Nishitani sum score was significantly increased in the DSS+vehicle group compared to the vehicle control (no DSS) group. Administration of the high dose of compound 1 (10000 nmol/kg) but not the low dose of compound 1 (1250 nmol/kg) from day −2 resulted in a significantly reduced whole colon inflammation severity score compared with the DSS+vehicle group (FIG. 7).

Together, these findings confirm a significant therapeutic effect of compound 1 on multiple disease activity parameters in the DSS induced colitis mouse model, including amelioration of disease activity index (DAI) score, reduction of colon shortening, reduced histological damage and inflammation severity in the colon.

Example 9

Chemical Stability of Compound 1, Comparative Compound 1 and Comparative Compound 2

Figure 8:
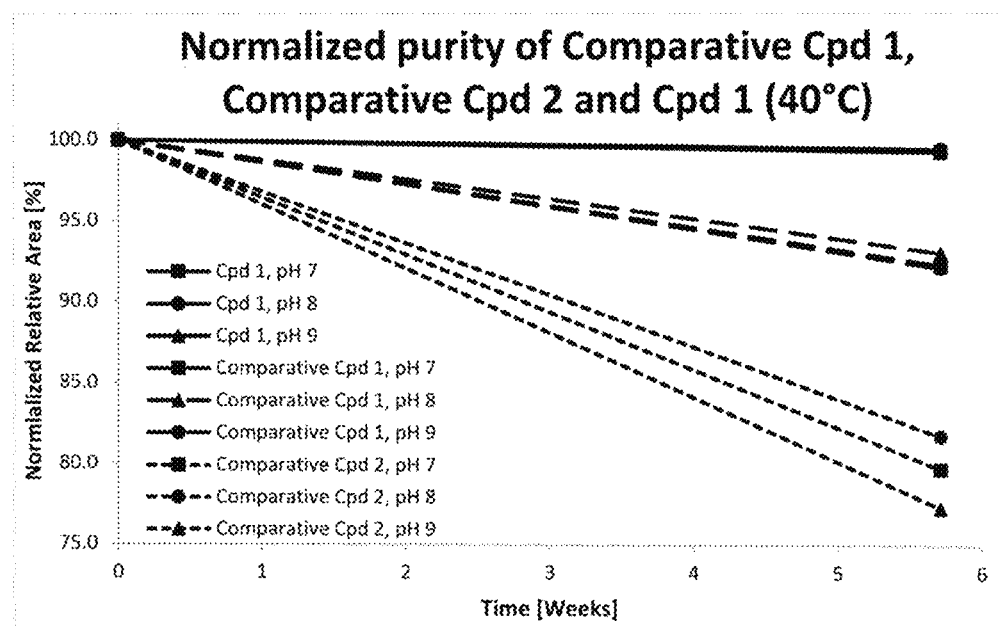
FIG. 8 shows the normalised purity values for compound 1 and comparative compounds 1 and 2 after 40 days' storage at 40° C., as determined by the method described in Example 9.

In this Example, the stability of Compound 1 was tested and compared with that of Comparative Compound 1 and Comparative Compound 2.
Materials and Method
The chemical stability of the compounds was tested under aqueous conditions at 1 mg/mL in 20 mM phosphate pH 7, 20 mM phosphate pH 8 and 20 mM glycine pH 9. Chemical stability was followed for the duration of two weeks at 40° C., using the normalized endpoint purity to assess chemical stability.
HPLC for Chemical Purity Determination
The formulated samples were measured on T=0 and 40 days by reverse phase HPLC using a conventional HPLC apparatus, such as a Dionex® Ultimate 3000 system, for binary gradient application equipped with a column, such as 1.5×150 mm Acquity UPLC peptide CSH column, and using a suitable gradient from buffer A (0.3% trifluoroacetic acid, aq.) and buffer B (0.3% trifluoroacetic acid, 90% MeCN, aq.), with a column temperature of 70° C. and a gradient from 20 to 80% MeCN over 49 minutes. Purity is determined as peak area.
Stock Solutions
The compound was carefully weighed out and dissolved in MQ water to 2 mg/mL and pH adjusted to neutral pH (pH 6-8). The stock solution was equilibrated 15 minutes at ambient temperature, at which point no visible particles were present. 40 mM buffer stock solutions were prepared for each pH condition tested.
Chemical Stability Assay
The formulations for chemical testing were made by mixing peptide stock and buffer stock in a ratio of 1:1. This was done for each buffer/pH condition in Protein LoBind tube 2.0 mL (Eppendorf). These samples were placed in a temperature-controlled chamber set to 40° C. for 40 days.
Measuring Chemical Stability
Chemical stability was assessed by taking out a small volume and running on the Dionex® Ultimate 3000 system. The generated chromatograms were integrated and normalized purity data generated by normalization against the freshly dissolved sample (T=0). The endpoint data after 40 days storage at 40° C. are reported below in Table 10 and shown in FIG. 8.

TABLE 10

| Compound | Formulation | Normalized purity after 40 days storage at 40° C. |
|---|---|---|
| Comparative Compound 1 | 20 mM phosphate pH 7 | 92 |
| Comparative Compound 1 | 20 mM phosphate pH 8 | 93 |
| Comparative Compound 1 | 20 mM glycine pH 9 | 92 |
| Comparative Compound 2 | 20 mM phosphate pH 7 | 80 |
| Comparative Compound 2 | 20 mM phosphate pH 8 | 82 |
| Comparative Compound 2 | 20 mM glycine pH 9 | 77 |
| Compound 1 | 20 mM phosphate pH 7 | 99 |
| Compound 1 | 20 mM phosphate pH 8 | 99 |
| Compound 1 | 20 mM glycine pH 9 | 99 |

Example 10

Chemical Stability of Compound 1 and Comparative Compound 1 in Dry Conditions In this Example, the stability of Compound 1 was tested and compared with that of Comparative Compound 1.

Materials and Method

The chemical stability of the compounds was tested under dry conditions. Chemical stability was followed for the duration of 3 months at 40° C. in a desiccator with a relative humidity set by an aqueous solution saturated with NaCl. Normalized endpoint purity is used to assess chemical stability.

HPLC for Chemical Purity Determination

The formulated samples were measured on T=0, 1, 2 and 3 months by reverse phase HPLC using a conventional HPLC apparatus, such as a Dionex® Ultimate 3000 system, for binary gradient application equipped with a column, such as 1.5×150 mm Acquity UPLC peptide CSH column, and using a suitable gradient from buffer A (0.3% trifluoroacetic acid, aq.) and buffer B (0.3% trifluoroacetic acid, 90% MeCN, aq.), with a column temperature of 50° C. and a gradient from 20 to 80% MeCN over 19 minutes. Purity is determined as peak area.

Stock Solutions

The compound was carefully weighed out and dissolved in Milli-Q® purified water (MQ water) to 2 mg/mL and pH adjusted as necessary to reach dissolution, which in the case of Compound 1 was pH 2-3 and Comparative Compound 1 pH 6. The stock solution was equilibrated 15 minutes at ambient temperature, at which point no visible particles were present.

Chemical Stability Assay:

Two dry formulations were generated for chemical stability testing. The first formulation was generated by diluting the compound stock to 1 mg/mL in MQ water with no further pH adjustment, and the second formulation is generated by diluting the stock to 1 mg/mL with MQ water and adjusting the pH to 9 using NaOH/HCl. These two formulations were aliquoted into Eppendorf tubes, and dry formulations generated by lyophilization. For chemical stability assessment, the formulations were stored at 40° C. in a desiccator with a relative humidity set by saturated NaCl solution.

Figure 9:
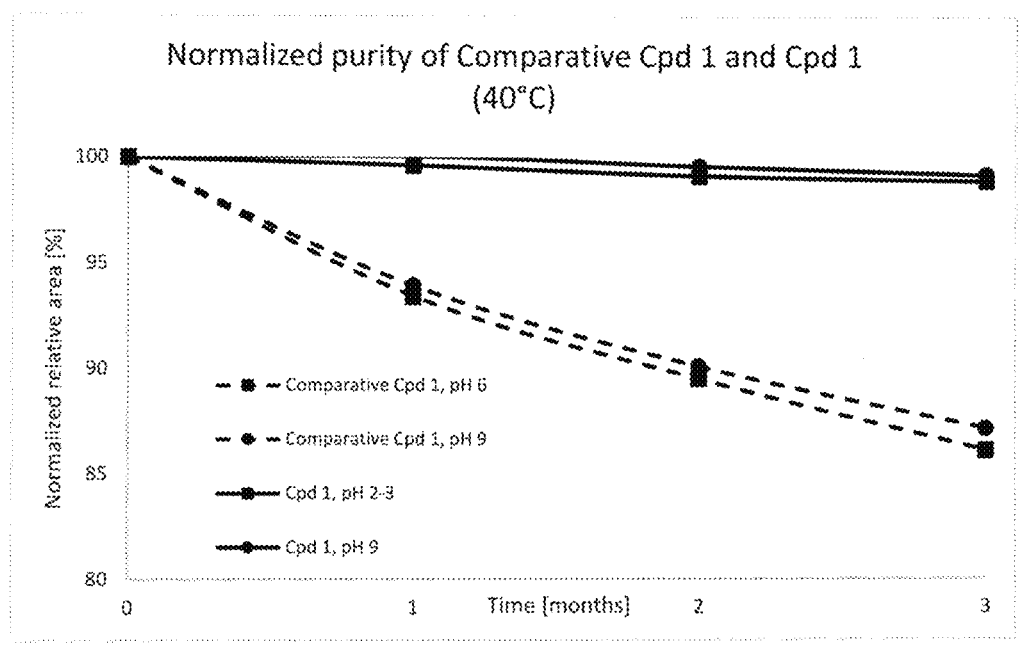
FIG. 9 shows the stability under dry conditions of compound 1 compared with comparative compounds 1 when tested according to the conditions described in example 10.

Measuring Chemical Stability:

Chemical stability was assessed by taking out one Eppendorf tube of each compound and formulation per pull point. 20 mM phosphate pH 7.0 was used to dissolve the dried formulation to a concentration of 1 mg/mL. The samples were then measured on a Dionex® Ultimate 3000 system. The generated chromatograms were integrated and normalized purity data generated by normalization against re-dissolved dry formulation generated on T=0. The endpoint data after 3 months storage at 40° C. are reported below in Table 11 and shown in FIG. 9.

Compound 1 and Comparative Compound 1 have both been tested for chemical stability in aqueous formulations (Example 9) and dry formulations (Example 10). The results show that Compound 1 has greater stability in both aqueous and dry formulations compared with Comparative Compound 1.

TABLE 11

| Compound | Formulation | Normalized purity after three months storage at 40° C. |
|---|---|---|
| Comparative Compound 1 | pH 6 | 86 |
| Comparative Compound 1 | pH 9 | 87 |
| Compound 1 | pH 2-3 | 99 |
| Compound 1 | pH 9 | 99 |

Example 11

Pharmacokinetic Characterisation of Compound 1, Comparative Compound 1 and Comparative Compound 2

Method

Sprague Dawley or Wistar rats (males with a body weight of approximately 250-350 g) were given a single intravenous (i.v. bolus) injection of the peptide to be tested. Following i.v. administration of compound 1 (dose 510 nmol/kg, dosing volume 2 mg/kg), blood samples were drawn at 10 min, 15 min, 40 min, 1 h, 2 h, 4 h, 7 h, 24 h, 30 h and 48 h post-dose. At each sampling time point, samples from the rats were drawn by tail cut. The dosing vehicle was 20 mM phosphate buffer, 260 mM mannitol, pH 7.

Plasma samples were analyzed after protein precipitation by liquid chromatography mass spectrometry (LC-MS/MS). Individual plasma concentrations were used for calculation of the pharmacokinetic parameters using the non-compartmental approach in Phoenix WinNonlin 8.3 or a later version. Plasma terminal elimination half-life (T½) was determined as $\ln(2)/\lambda z$ where $\lambda z$ is the magnitude of the slope of the log linear regression of the log concentration versus time profile during the terminal phase. $AUC_{inf}$ is the area under the plasma concentration–time curve extrapolated to infinity ($AUC_{inf}=AUC_{last}+C_{last}/\lambda z$, where $C_{last}$ is the last observed plasma concentration). $C_0$ is the plasma concentration at the dosing time intercept and is back extrapolated by log-linear regression of the first two data points.

The results for selected compounds are shown in table 12.

TABLE 12

| Compound | Dose nmol/kg | $AUC_{inf}$ (hr*nmol/L) | $C_0$ (nmol/L) | $T_{1/2}$ (hr) |
|---|---|---|---|---|
| Compound 1 | 511 | 34000 | 9020 | 7.88 |
| Comparative Compound 1 | 511 | 4640 | 2900 | 2.39 |
| Comparative Compound 2 | 511 | 13500 | 4940 | 7.58 |

All publications mentioned in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications and equivalents of the described modes for carrying out the invention which are obvious to those skilled in chemistry, pharmacy or related fields are intended to be within the scope of the following claims.

The invention claimed is:
1. A compound of formula (I):
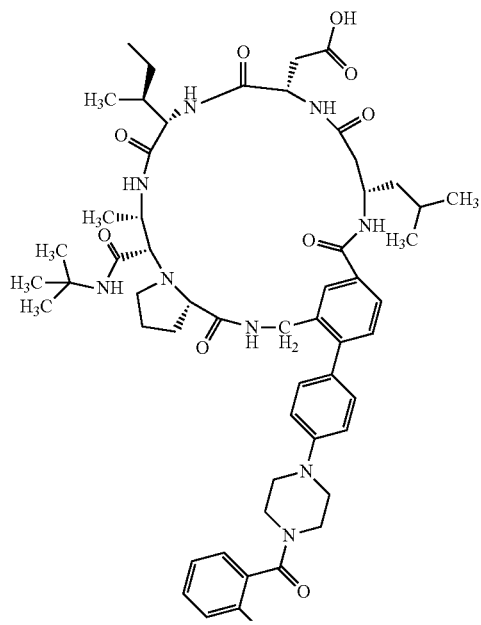
(I)
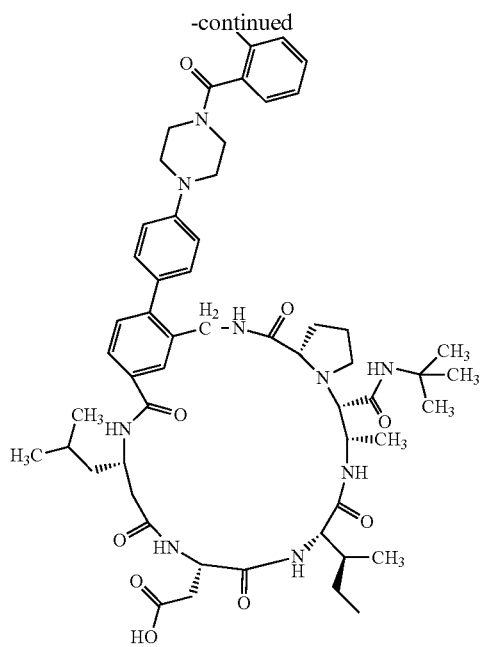
or a pharmaceutically acceptable salt or solvate thereof.
2. A pharmaceutical composition comprising the compound or pharmaceutically acceptable salt or solvate thereof of claim 1 and a pharmaceutically acceptable carrier.
* * * * *